United States Patent [19]
Modell et al.

[11] Patent Number: 5,813,987
[45] Date of Patent: Sep. 29, 1998

[54] SPECTRAL VOLUME MICROPROBE FOR ANALYSIS OF MATERIALS

[75] Inventors: Mark Modell, Brookline; Gregory DeBaryshe, Lincoln, both of Mass.; A. Ze'ev Hed, Nashua, N.H.

[73] Assignee: MediSpectra, Inc., Lexington, Mass.

[21] Appl. No.: 778,039

[22] Filed: Dec. 24, 1996

Related U.S. Application Data

[63] Continuation of Ser. No. 510,043, Aug. 1, 1995, abandoned.

[51] Int. Cl.$^6$ ........................................................ A61B 6/00
[52] U.S. Cl. ........................... 600/473; 600/476; 250/216
[58] Field of Search ..................................... 356/342, 338; 600/178, 180, 181, 473, 476, 310; 250/216, 578.1

[56] References Cited

U.S. PATENT DOCUMENTS

| Re. 34,214 | 4/1993 | Charlsson et al. | 358/93 |
|---|---|---|---|
| 3,013,467 | 12/1961 | Minsky | 88/14 |
| 4,017,192 | 4/1977 | Rosenthal | 356/201 |
| 4,198,571 | 4/1980 | Sheppard | 250/571 |
| 4,254,421 | 3/1981 | Kreutel, Jr. | 343/754 |

(List continued on next page.)

FOREIGN PATENT DOCUMENTS

| 1223092 | 4/1986 | U.S.S.R. . |
|---|---|---|
| WO 94/26168 | 11/1994 | WIPO . |

OTHER PUBLICATIONS

N. Ramanujam et al, "In vivo diagnosis of cervical intraepithelial neoplasia using 337–nm–excited laser–induced fluorescence", Proc. Natl. Acad. Sci. USA, vol. 91, pp. 10193–10197, Oct. 1994.

N. Ramanujam et al, Fluorescence Spectroscopy: A Diagnostic Tool for Cervical Intraepithelial Neoplasa (CIN), Gynecologic Oncology 52, pp. 31–38 (1994).

Kevin T. Schomacker, et al, "Ultraviolet Laser–Induced Fluorescence of Colonic Tissue: Basic Biology and Diagnostic Potential", Lasers in Surgery and Medicine, 12: 63–78, (1992).

Jeffrey W. Hall, et al, "Near–Infrared Spectrophotometry: A New Dimension in Clinical Chemistry", Clin. Chem. 38/9, 1623–1631 (1992).

R. Richards–Kortum et al, "Description and Performance of a Fiber–Optic Confocal Fluorescence Spectrometer", Applied Spectroscoy, vol. 48, No. 3, pp. 350–355, (1994).

S. Schwartz, "Real–time laser–scanning confocal ratio imaging", American Laboratory, pp. 53–62, Apr. 1993.

P. Davidovits et al, "Scanning Laser Microscope for Biological Investigations", Applied Optics, vol 10, No. 7, pp. 1615–1619, Jul. 1971.

(List continued on next page.)

*Primary Examiner*—George Manuel
*Assistant Examiner*—Shawna J. Shaw
*Attorney, Agent, or Firm*—Wolf, Greenfield & Sacks, P.C.

[57] ABSTRACT

An optical probe collects light emanating from a specimen that selectively andpreferentially represents a localized volume element within the sample, with illuminationintensity and collection efficacy both dropping off away from the localized volume element to limit the integrated contribution from outside the element. For example, the optics provide high peak illumination and high collection efficiency which both overlap in volume elements of a limited size corresponding to a structure or process of the specimen. The resulting collected signal comprising one or more spectral segments is highly correlated with optical characteristics, such as absorbance, scattering or fluorescence characteristics of material in the small volume elements. A processor may apply a previously-derived vector or matrix transform to the collected responses to produce an output. The collected spectra or other responses have high signal strength and represent small or otherwise inaccessible or masked optical effects present in the sample, so that they are readily correlated to conditions of interest.

25 Claims, 19 Drawing Sheets

U.S. PATENT DOCUMENTS

| | | | |
|---|---|---|---|
| 4,357,075 | 11/1982 | Hunter | 350/294 |
| 4,397,557 | 8/1983 | Herwig et al. . | |
| 4,733,063 | 3/1988 | Kimura et al. | 250/201 |
| 4,753,530 | 6/1988 | Knight et al. | 356/73 |
| 4,844,617 | 7/1989 | Kelderman et al. | 356/372 |
| 4,845,352 | 7/1989 | Benschop | 250/201 |
| 4,852,955 | 8/1989 | Doyle et al. | 350/1.2 |
| 4,930,513 | 6/1990 | Alfano et al. | 128/665 |
| 4,965,441 | 10/1990 | Picard | 250/201.3 |
| 4,972,258 | 11/1990 | Wolf et al. | 358/93 |
| 4,997,242 | 3/1991 | Amos | 350/6.91 |
| 5,011,243 | 4/1991 | Doyle et al. | 350/1.2 |
| 5,028,802 | 7/1991 | Webb et al. | 250/571 |
| 5,032,720 | 7/1991 | White | 250/236 |
| 5,034,613 | 7/1991 | Denk et al. | 250/458.1 |
| 5,042,494 | 8/1991 | Alfano | 128/665 |
| 5,054,926 | 10/1991 | Dabbs et al. | 356/345 |
| 5,065,008 | 11/1991 | Hakamata et al. | 250/216 |
| 5,071,246 | 12/1991 | Blaha et al. | 351/221 |
| 5,074,306 | 12/1991 | Green et al. . | |
| 5,083,220 | 1/1992 | Hill | 359/234 |
| 5,091,652 | 2/1992 | Mathies et al. | 250/458.1 |
| 5,120,953 | 6/1992 | Harris | 250/227.2 |
| 5,122,653 | 6/1992 | Ohki | 250/216 |
| 5,132,526 | 7/1992 | Iwasaki | 250/201.3 |
| 5,139,025 | 8/1992 | Lewis et al. . | |
| 5,161,053 | 11/1992 | Dabbs | 359/384 |
| 5,162,641 | 11/1992 | Fountain | 250/201.2 |
| 5,162,941 | 11/1992 | Favro et al. | 359/386 |
| 5,168,157 | 12/1992 | Kimura | 250/234 |
| 5,192,980 | 3/1993 | Dixon et al. | 356/326 |
| 5,201,318 | 4/1993 | Rava et al. | 128/665 |
| 5,225,671 | 7/1993 | Fukuyama | 250/216 |
| 5,235,457 | 8/1993 | Lichtman et al. | 359/368 |
| 5,239,178 | 8/1993 | Derndinger et al. | 250/234 |
| 5,248,876 | 9/1993 | Kerstens et al. | 250/561 |
| 5,260,569 | 11/1993 | Kimura | 250/234 |
| 5,260,578 | 11/1993 | Bliton et al. | 250/461.1 |
| 5,262,646 | 11/1993 | Booket et al. | 250/341 |
| 5,274,240 | 12/1993 | Mathies et al. | 250/458.1 |
| 5,286,964 | 2/1994 | Fountain | 250/201.2 |
| 5,294,799 | 3/1994 | Aslund et al. | 250/458.1 |
| 5,296,700 | 3/1994 | Kumagai | 250/216 |
| 5,303,026 | 4/1994 | Strobl et al. | 356/318 |
| 5,306,902 | 4/1994 | Goodman | 250/201.3 |
| 5,313,567 | 5/1994 | Civanlar et al. | 395/124 |
| 5,318,200 | 6/1994 | Rosenthal et al. | 250/341 |
| 5,324,979 | 6/1994 | Rosenthal | 250/504 R |
| 5,329,352 | 7/1994 | Jacobsen | 356/301 |
| 5,343,038 | 8/1994 | Nishiwaki et al. | 250/234 |
| 5,345,306 | 9/1994 | Ichimura et al. | 356/346 |
| 5,421,337 | 6/1995 | Richards-Kortum et al. | 128/665 |
| 5,451,931 | 9/1995 | Müller et al. . | |

OTHER PUBLICATIONS

C. Koester, "Comparison of Optical Sectioning Methods: The Scanning Slit Confocal Microscope", Confocal Microscopy Handbook, pp. 189–194.

J.M. Schmitt et al, "Confocal Microscopy in Turbid Media", Biomed. Eng. And Inst. Program, NCRR, National Institute of Health, Bethesda, MD 20892, pp. 1–46.

S.G. Anderson, "Confocal Laser Microscopes See A Wider Field of Application", Laser Focus World, pp. 83–86, Feb. 1994.

T. Wilson, "The Role of th Pinhole in Confocal Imaging Systems", Confocal Microscopy Handbook, pp. 99–113.

C.J.R. Sheppard et al, "Depth of Field in the Scanning Microscope", Optics Letters, vol. 3, No. 3 Sep. 1978, pp. 115–117.

C. J. Koester, "Scanning Mirror Microscope with Optical Sectioning Characteristics: Applicaitons in Ophthalmology", Applied Optics, vol. 19, No. 11, Jun. 1980, pp. 1749–1757.

J.M. Schmitt et al, "Interferometric Versus Confocal Techniques for Imaging Microstructures in Turbid Biologocal Media", Proc. SPIE, 2135 (1994), pp. 1–12.

5,813,987

SPECTRAL VOLUME MICROPROBE FOR ANALYSIS OF MATERIALS

This application is a continuation of application Ser. No. 08/510,043, filed Aug. 1, 1995 now abandoned.

BACKGROUND OF THE INVENTION

This invention relates to improved means and methods for deriving spatiallydifferentiated analytic information from a specimen by analyzing the results of theinteraction of electromagnetic radiation with the specimen, and in particular to new and useful devices and methods of using data generated by such devices to provide in vivo diagnostic information on said specimen. This is achieved by spatially limiting a probing electromagnetic beam to have maximum power density within a small volume element and limiting the accepted response detected to essentially only the same volume element.

A significant need exists for an instrument capable of automatically providing a rapid analysis, for example, of cancerous, diseased, or otherwise injured tissue. In particular, there remains a need for instruments capable of accurately diagnosing the size and stage of cancerous growth or otherwise injured tissue. Today, the medical field generally relies on visual analysis and tissue biopsies to analyze biological tissue for specific pathologies and abnormalities. Various forms of biochemical imaging are used as well, and finally, the optical response of various pathologies are being used in attempts to characterize biological tissues. These prior art techniques, however, contain serious drawbacks.

For example, performing a tissue biopsy and analyzing the extracted tissue in the laboratory requires a great deal of time. In addition, tissue biopsies can only characterize the tissue based upon representative samples taken from the tissue. This results in a large number of resections being routinely performed to gather a selection of tissue capable of completely representing the sample. In addition tissue biopsies are subject to sampling and interpretation errors. Magnetic resonance imaging is a successful tool, but it is expensive and has serious limitations in detecting pathologies that are very thin or in their early stages of development.

One technique used in the medical field for tissue analysis is induced fluorescence. Laser induced fluorescence utilizes a laser tuned to a particular wavelength to excite tissue and to cause the tissue to fluoresce at a set of secondary wavelengths that can then be analyzed to infer characteristics of the tissue. Fluorescence can originate either from molecules normally found within the tissue, or from molecules that have been introduced into the body to serve as marker molecules.

Although the mechanisms involved in the fluorescence response of biological tissue to UV excitation have not been clearly defined, the fluorescence signature of neoplasia appears to reflect both biochemical and morphological changes. For example, useful auto-fluorescence spectral markers may reflect biochemical changes in the mitochondria, e.g., in the relative concentration of reduced nicotinamide adenine dinucleotide (NADH) and flavins. Mucosal thickening and changes in capillary profusion are structural effects that have been interpreted as causing some typical changes in the spectroscopic record.

The major molecules in biological tissue which contribute to a fluorescence emission response to 337 nm near-UV light excitation, have been identified as tryptophan (390 nm emission), chromophores in elastin (410 nm) and collagen (300 nm), NADH (470 nm), flavins (520 nm) and melanin (540 nm). It should be noted, however, that in tissue, there is also some peak shifting and changes in the overall shape relative to the pure compounds. Accordingly, the sample can be illuminated with a UV beam of sufficiently short wavelength and responses recorded from the above enumerated wavelengths of light in order to determine the presence of each of above identified contributions to tissues types.

It has been further shown that hemoglobin has an absorption peak between 400 and 540 nm, while both oxyhemoglobin and hemoglobin have strong light absorption above 600 nm. Blood distribution may also influence the observed emission spectra of elastin, collagen, NAD, and NADH. Further compounds present in tissue which may absorb emitted light and change the shape of the detected emission spectra include myoglobin, porphyrins, and dinucleotide co-enzymes.

Among other general background, we note a general belief that neoplasia has high levels of NADH because its metabolic pathway is primarily anaerobic. The inability of cells to elevate their NAD+:NADH ratio at confluence is a characteristic of transformed cells related to their defective growth control. The ratio of NADH+:NADH is an indicator of the metabolic capability of the cell, for example, its capacity for glycolysis versus gluconeogenesis. Surface fluorescence has been used to measure the relative level of NADH in both in vitro and in vivo tissues. Emission spectra obtained from individual myocytes produces residual green fluorescence probably originating from mitochondrial oxidized flavin proteins, and blue fluorescence is consistent with NADH of a mitochondrial origin.

Collagen, NADH, and flavin adenine dinucleotide are thought to be the major fluorophores in colonic tissue and have been used to spectrally decompose the fluorescence spectra. Residuals between the fits and the data resemble the absorption spectra of a mix of oxy-and deoxy-hemoglobin; thus the residuals can be attributed to the presence of blood.

Alfano, U.S. Pat. No. 4,930,516, teaches the use of luminescence to distinguish cancerous from normal tissue when the shape of the visible luminescence spectra from the normal and cancerous tissue are substantially different, and in particular when the cancerous tissue exhibits a shift to the blue with different intensity peaks. For example, Alfano discloses that a distinction between a known healthy tissue and a suspect tissue can be made by comparing the spectra of the suspect tissue with the healthy tissue. According to Alfano, the spectra of the tissue can be generated by exciting the tissue with substantially monochromatic radiation and comparing the fluorescence induced at at least two wavelengths.

Alfano, in U.S. Pat. No. 5,042,494, teaches a technique for distinguishing cancer from normal tissue by varying the excitation wavelength and observing differences in the shapes of the visible luminescence spectra for normal and cancerous tissue. Alfano further teaches, in U.S. Pat. No. 5,131,398, the use of luminescence to distinguish cancer from normal or benign tissue by employing (a) monochromatic or substantially monochromatic excitation wavelengths below the visible band at about 315 nm, and, in particular, between about 260 and 315 nm, and, specifically, at 300 nm, and (b) comparing the resulting luminescence at two wavelengths about 340 and 440 nm. While clearly defined color differences in certain dense tumor tissue are diagnostically useful, the approach does not distinguish between normal, malignant, benign, tumorous, dysplastic, hyperplastic, inflamed, or infected tissue. Inability to define these subtle distinctions in diagnosis would make appropriate treatment choices nearly impossible. While the simple ratio, difference and comparison analysis of Alfano and others offer promise for development as useful tools in cancer research and provocative indicators of tissue status, more effective methods are required to provide accurate and robust clinical tools.

It is quite evident from the above that the actual spectra obtained from biological tissues are extremely complex and thus difficult to resolve by standard peak matching programs, spectral deconvolution or comparative spectral analysis. Furthermore, spectral shifting further complicates such attempts at spectral analysis. Last, laser fluorescence and other optical responses from tissues typically fail to achieve depth resolution because either the optical or the electronic instrumentation commonly available for these techniques entails integrating the signal emitted by the excited tissue over the entire illuminated tissue volume.

Rosenthal, U.S. Pat. No. 4,017,192, describes a technique for automatic detection of abnormalities, including cancer, in multi-cellular bulk biomedical specimens, which overcomes the problems associated with complex spectral responses of biological tissues. Rosenthal teaches the determination of optical response (transmission or reflection) data from biological tissue over a large number of wavelengths for numerous samples and then the correlation of these optical responses to conventional, clinical results to select a few test wavelengths and a series of constants to form a correlation equation. The correlation equation is then used in conjunction with optical responses at the selected wavelengths taken on an uncharacterized tissue to predict the status of this tissue. However, to obtain good and solid correlations, Rosenthal excises the tissues and obtains in essence a homogeneous sample in which the optical responses do not include the optical signatures of underlying tissues. Rosenthal's methods, therefore, cannot be used in in vivo applications as contemplated in the present invention.

In studies carried out at the Wellman Laboratories of Photomedicine, using a single fiber depth integrating probe, Schomacker has shown that the auto-fluorescence of the signature of human colon polyps in vivo can be an indicator of four different states: normality, benign hyperplasia, pre-cancerous, and malignant neoplasia. See Schomacker et al., *Lasers Surgery and Medicine,* 12, 63–78 (1992), and *Gastroenterology* 102, 1155–1160 (1992). Schomacker further teaches using multi-variant linear regression analysis of the data to distinguish neoplastic from non-neoplastic polyps. However, using Schomacker's techniques, the observation of mucosal abnormalities was substantially impaired by the signal from the submucosa, since 87% of the fluorescence observed in normal colonic tissue can be attributed to submucosal collagen. An instrument which could discriminate the sources in depth would improve performance.

Accordingly, there is a need for a more effective and accurate device to characterize specimens, and particularly in vivo specimens, which will obtain responses from well defined volume elements within the specimens, and furthermore, there is a need for methods to automatically interpret such data in terms of simple diagnostic information about the volume elements.

It is therefore the main object of the instant invention to provide methods and means to analyze a sample by inducing interaction between electromagnetic radiation and a defined, controllable, and localized volume element within a sample and spatially restricting the response observed to this small volume element.

It is also an object of this invention to provide means for analyzing volume elements of material emanating weak or spatially masked signals, such as a volume element of material located below a proximal plane or surface of the specimen being analyzed, or above a plane that emits interfering signals.

It is an additional object of the instant invention to provide means for automatically determining the nature and/or the pathological state of biological tissues, by measuring the response of discrete volume elements in the tissues to an exciting beam and correlating the responses to responses of known pathologies, or to ensembles of pathology responses and extrinsic medical data.

It is yet another object of the invention to provide in vivo diagnostic information for tissues that are directly observable, or tissues that are accessible optically either by direct observation or through rigid or flexible optical paths such as laparoscopes or endoscopes.

It is a further object of the invention to rapidly analyze or detect regions of cancerous, diseased, or otherwise injured tissue with a high degree of accuracy and at low cost.

It is a further object of the invention to monitor tissue to determine whether organ or skin grafts are viable.

It is further object of the invention to measure oxygen perfusion, hemoglobin, other metabolites, and tissue or blood chemicals in vivo.

It is a further object of the invention to monitor temporal and spatial distribution of drugs, especially, drugs used in photodynamic therapy.

Further objects of the invention include analyzing volume elements of a tissue whose size is clinically significant to a physician.

These and other objects will be apparent from the description that follows.

SUMMARY OF THE INVENTION

In its broadest terms, the invention provides an instrument for eliciting and detecting a response to radiation from delineated regions of a sample such as tissue, which is, intuitively speaking, a strong and "pure", or undiluted response. While particle beams have proven highly effective for qualitative microanalysis of materials (e.g., chemical elements and metalized microstructure) that can be probed by point-like high energy scanning, the situation is far different for attempts to elicit responses to lower energy radiation from more complex systems in more transparent media, such as organic materials in living systems, or chemical reactions in fluids. For example, acoustic (e.g. compressional wave) radiation and photonic radiation both suffer from a number of noise-introducing drawbacks which include scattering, mode-conversion, absorption and reemission, and a number of related or analogous effects such that collected responses to such radiation become diluted, impure, filtered or otherwise substantially altered by unrelated noise from spatially neighboring regions or from physically co-located but substantively uninteresting intermixed material. The invention solves this drawback by a probe which stimulates and collects responses from a volume element such as a layer of tissue, a localized growth, or a reaction volume that is delineated in accordance with an active process. In general, this is achieved by arranging that the stimulation beam, such as an illumination beam, has a defined irradiance distribution that falls greatly outside a first region, and that the instrumentation for collecting responses to the stimulation has a collection efficiency that has similar spatial discrimination about a second region, with the first and second regions intersecting to define the probed volume element. Thus a volume element is defined by the overlapping spatial distributions of stimulation and of detection sensitivity.

The invention is most readily understood using as an example the illumination of a sample and collection of light from the sample, and accordingly in the following description the terms "light", "illumination" or "radiation" shall be used throughout. However, it is applicant's intention that the foregoing terms, both in the disclosure and in the claims appended hereto, shall be understood to mean and include any form of electromagnetic radiation that may be formed into beams and focused or otherwise shaped or spatially distributed using field stops, apertures and focusing elements, and also to include acoustic radiation.

In order to more completely define and describe the invention herein, certain terms are defined as set forth below. The invention contemplates the use of field stops which are large compared to the resolution of the illuminating and collecting path objective lenses, respectively, yet which are used in configurations that together strongly define localized volume elements from which responses are collected. Applicants have found the most useful quantitative definitions of this aspect of the invention to involve the concepts of encircled power and comparative spot size. In the absence of diffraction, images could be precisely predicted by geometrical optics, including the effects of aberrations; the concept of comparative spot size uses a comparison of the size of an image predicted by geometric optics with the image predicted when diffraction is properly taken into account or when the image is accurately measured in the presence of diffraction effects and residual aberrations. Encircled power is the fraction of the total optical flux in an image surface that is found within a stated boundary, for example, the geometric image. Furthermore, resolution will vary with the position of an image with respect to the principal points of the optical system; therefore, when accurately defined, the definition will include the location at which the resolution is specified, which is here taken to be in the plane of the field stop. For the purposes of this specification and its associated descriptions and claims, the terms "large field stop", "field stop larger than the diffraction limited spot", and "field stop larger than the classical resolution of its objective" mean a field stop which is large compared to the size of the image of a point object formed by an associated well-corrected objective when that point object is so disposed that its image falls on the location of the field stop.

A "volume-microprobe" or "volume-microprobe configuration" or "weakly confocal configuration" means 1) a configuration which employs radiation to characterize a sample, and
    a) which uses a pair of field stops in the illuminating, and collecting paths, wherein the field stops are larger than the classical resolution at those field stops of their associated objectives, and
    b) in which the field stops are conjugated at least in part through a common volume element of a sample, and
    c) employs the observed radiation to characterize the common volume element; or
2) a configuration in which the illuminating and collecting field stops are physically the same stop. A "volume-probe" means
1) a volume-microprobe configuration; or
2) any configuration which employs radiation to characterize a sample, and
    a) limits the volume element from which information is extracted to a sub-volume of the illumination and observation paths, and
    b) thereby discriminates against radiation emanating outside said limited volume element, and
    c) limits the volume element to less than the entire volume of the sample, and
    d) permits predetermination and at least partial control of the size and location of said volume element to effectively discriminate between locations within the sample.

Similarly, the term "optical" and "radiation" shall include both electromagnetic and acoustic optics and radiation, and "volume-element" shall refer generally to a localized volume defined by the optical configuration.

In general, instruments embodying the invention operate by collecting an optical response from a defined volume element, detection of this response forming a "record" which may be either permanent or ephemeral. The record may, for example, be an electrical signal from a photodetector or from a detector processing circuit, may be a visual display on a display screen, or may be a mathematically quantified measurement or set of measurements stored in a memory or hard record form.

The discussion below shall for simplicity generally assume an "ideal" medium, i.e., a medium in which scattering or effects dependent on index of refraction of that medium do not sensibly affect the propagation of light therein.

Turning now to a representative instrument, the objectives of the invention are achieved by providing two optical assemblies which conjugate their field stops via the volume element from which the optical response is sought. The first optical assembly is designed to image a field stop which selectively transmits a beam from a light source, or other source of radiation, into a volume element. The second optical assembly is designed to collect light or radiation emanating from the target volume element, and largely only from the element, and transmit the light or radiation to a detector for further analysis of the interaction of the first transmitted beam with the volume element. The first optical assembly includes a field stop to achieve selective illumination of the selected volume element and the second optical assembly includes a second field stop to restrict acceptance of the emanating radiation or light into the collection optics, to that from the target volume element. Furthermore, a controller is provided, which in some embodiments of the instant invention, adjusts the depth of the selected volume element relative to the surface of the specimen by controlling the respective image regions of the two optical assemblies while keeping their conjugation and having the sampled volume element as a common conjugation point for both assemblies. The general dimensions of these field stops are always large in order to sample, or process, physiologically interesting volume elements and are thus larger than the classical resolution of their objectives. The images of the field stops formed by the respective objectives of the two assemblies in the sampled volume element encompass substantially all (e.g., preferably more than 95%) of the flux passing through the non diffraction limited (geometric) images of the respective field stops, with appropriate correction for losses in the optics and the specimen. The field stops' dimensions may be selected to define sample volume elements that include a physiologically meaningful size of tissue which encompasses at least a few cells.

In some embodiments of the invention, the illuminating and collection optics are the same elements and filtering or beam splitting is used to separate the illuminating beam from the collected beam.

A configuration in which the illumination and collection field stops are conjugated is generally considered a confocal arrangement, whereby the field stops' images formed by the optical assemblies (the illuminating and the collecting assemblies) overlap within the object being viewed. Confocal arrangements in which the field stops are small "pinholes" (so that diffraction effects govern the depth discrimination) are well known in the prior art. For example, the confocal microscope disclosed in U.S. Pat. No. 3,013,467 issued to Marvin Minsky, provides for a double focusing, or "confocal" device having two optically conjugate pinhole field stops, which improves the contrast of images formed by rejecting substantially all received light originating outside the diffraction limited focal volume, i.e., by controlling the lateral field-of-view and by minimizing the effective depth of field surrounding the image surface. The data obtained from any single such point is of little utility and in a confocal microscope only the relative responses of a plurality of points, usually obtained by laterally scanning the sample, provide the desired high contrast two-dimensional image.

In the present invention, by contrast, the field stops define a volume element with dimensions much larger than the diffraction limited spots of the illuminating and collecting objectives and data obtained from a single volume element contains a clean spectral signal that is used for its diagnostic information. Indeed, while confocal microscopes obtain images of target surfaces by the convolution of optical responses obtained from a large number of closely spaced points in a sample, the instant invention can be described as a non imaging volume microprobe, in that no image of the sampled specimen need be obtained, but significant analytic data are obtained from discrete volume elements sampled. In other words, we are interested in optimizing the amount of absolute optical response energy (signal) obtained from a finite volume element, while in classical confocal microscopy the enhanced contrast in the response from a plurality of sub-microscopic point-like sources is the desired end. As a result of these opposite goals, confocal microscopy must use at least one field stop that is smaller than the classical resolution of its objective, and obtain readings from a plurality of adjacent points, while we use field stops that are much larger than the diffraction limited spot sizes of their objectives and obtain useful responses from single volume elements. The use of large field stops produces volume-limited responses many orders of magnitude stronger, and fundamentally alters the signal-to-noise ratio of collected light, allowing detection and rapid measurement of phenomena by their optical signatures that often cannot be even observed by confocal microscopy. By way of contrast, the inherent depth discrimination of the confocal microscope, that is its depth of field or depth of its diffraction limited focal volume element, depends on the wavelength of the illuminating light and on the nature of the interaction of that light with the sample; whereas the inherent depth discrimination in the present invention depends solely on the geometric parameters of the optical system.

The optical responses from the selected volume elements bear important information about the volume elements, such as the chemical, morphological, and in general the physiological nature of the volume elements. When the sample is spectrally simple, these optical responses may be analyzed by classical spectral techniques of peak matching, deconvolution or intensity determination at one or more selected wavelengths. One such system could be for example, a system for the determination of the degree of homogeneity of a mixture or a solution of a plurality of compounds. However, when the samples are complex biological specimens, as mentioned above, the spectral complexity observed with prior art instruments is often too great to obtain meaningful diagnosis. When such biological specimens are analyzed for subtle characteristics, we surprisingly found that the application of correlation transforms to spatially filtered optical responses obtained from discrete volume elements, or the use of such transforms in conjunction with data obtained through non imaging microscopy, yields diagnostically meaningful results.

A method of practicing this aspect of the invention is as follows, we first select a training set or sample of a specific target pathology; such a sample preferably has at least ten specimens. Optical responses are first collected from well defined volume elements in the specimens and recorded. The same volume elements that have been sampled with the non imaging volume microprobe of the instant invention are excised and biopsied. That is, histopathological analysis of the excised volume elements is carried out in a pathology laboratory, and the specimens are scored on an arbitrary scale (e.g. from zero to ten) which relates to the extent of the pathology, C (for instance a specific cancer) being characterized. These scores, $C_j$, where $C_j$ is the score value assigned to the specimen j within the training set, should be as accurate as possible, and thus an average of a number of pathologists' scores (determined on the same volume elements, j, can be used). We now create a set of equations $\Sigma a_{ic} F(I_{ij}) = C_j$, where i designates a spectral window (usually between 5 to 50 nm) and $F(I_{ij})$ is a specific function of the measured response intensity or other characteristics of the spectral response in the window i for volume element j. The function F may sometimes be the response intensity itself, in that window, namely, $F(I_{ij}) = I_{ij}$, or $F(I_{ij}) = (dI_{ij}/d\lambda)/I_{ij}$, where $\lambda$ is the median wavelength in the window i, or other functions. The factors $a_{ic}$ the correlation transforms coefficients for the pathology C, are now found from the set of equations created above, by applying well known numerical methods, such as multivariate linear regression analysis. In such analysis the number of wave length windows i required to obtain faithful correlations between the optical responses and the pathological derivations of the values $C_j$, is minimized and the set of correlation coefficients $a_{ic}$ for the pathology C are found. When we now record responses $(I_{ik})$, which form a vector in the space of i optical windows, minimized to a limited number of discrete elements from a sample outside the said training set and apply the transform operator $(a_{ic})$ on the vector $F(I_{jk})$, namely obtain the sum $\Sigma a_{ic} F(I_{ik}) = C_k$, result is a "score" quantifying the target pathology C for the volume element sampled.

Instruments embodying the invention are deemed useful for characterizing turbid materials, such as biological tissue, water, plastics, coatings, and chemical reaction processes, and may offer particular benefits in analysis of biological tissue, both in vitro and in vivo. To provide internal analysis, the invention is adapted to work with existing types of rigid and flexible endoscopes. The invention can be adapted by connecting the first and second optical elements with optical fibers to either an endoscope, laparoscope, or arthroscope.

BRIEF DESCRIPTION OF THE DRAWINGS

For a more complete understanding of the nature and objects of the invention, reference should be made to the following detailed description and the accompanying drawings, in which.

DETAILED DESCRIPTION OF THE INVENTION

Figure 1:
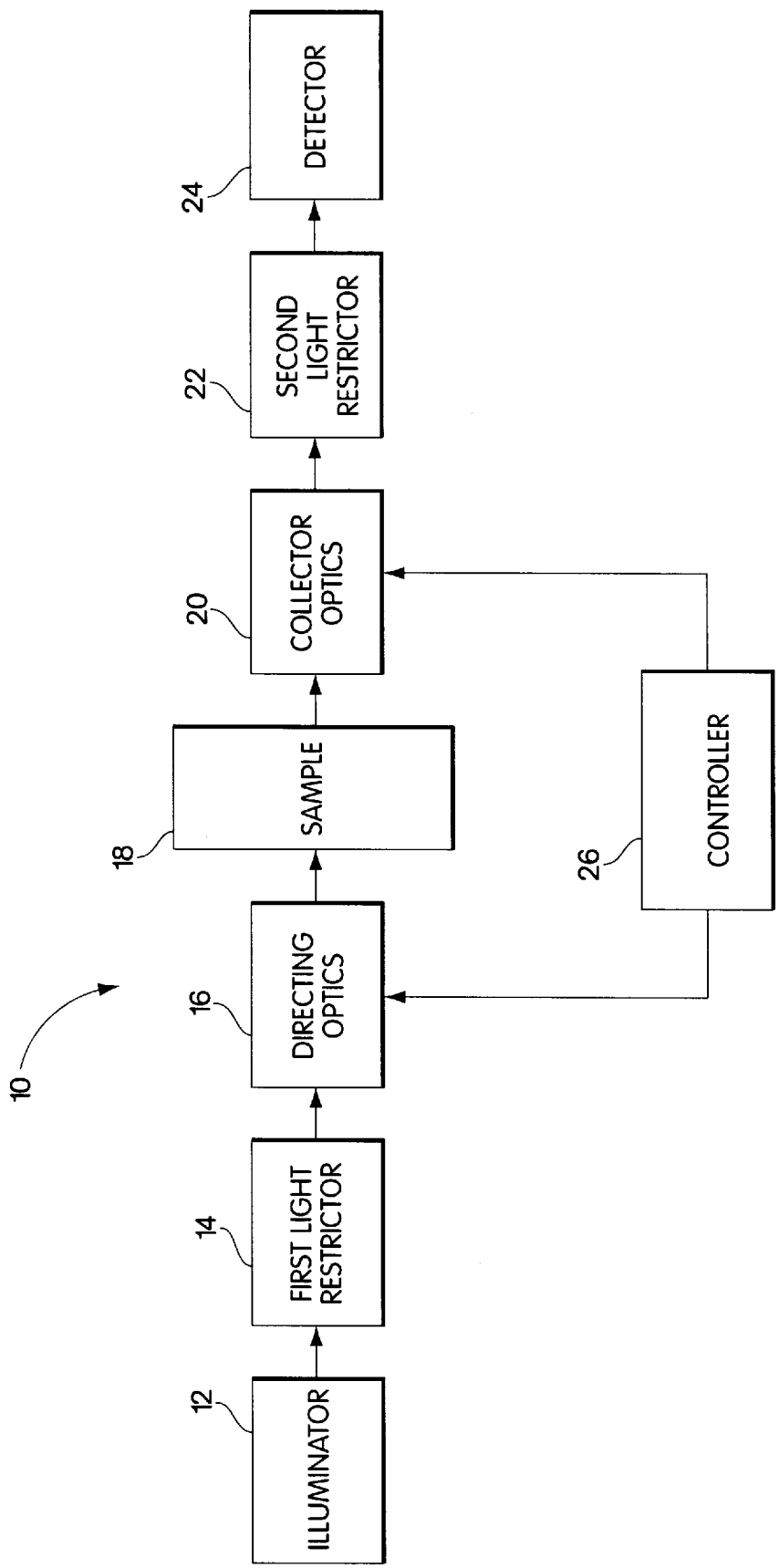
FIG. 1 shows a block diagram of a volume probing system according to the present invention.

FIG. 1 shows a volume probing system 10 according to the invention for illuminating a volume element in a sample 18 and for detecting radiation emanating from an illuminated target volume element in sample 18. The radiation emanating from the volume element is modified in a number of aspects relative to the impinging radiation, and is herein termed the "optical response" or simply, the "response" of the volume element sampled. These modifications carry the unique "signature" of the volume element sampled and can be correlated to chemical, morphological, physical and physiological characteristics of the volume element. The optical response can take the form of any one or a combination of the responses of matter irradiated by electromagnetic radiation, including reflection, transmission, selective absorption, various forms of scattering, various form of luminescence, and particularly fluorescence.

The system 10 has an illuminator 12 for generating radiation, a first light restrictor 14, and directing (objective) optics 16, collectively, the illuminating optics, for illuminating sample 18 with a beam formed of the radiation passed by the light restrictor 14. Probing system 10 also includes collector optics 20 (collection objective), a second light restrictor 22, and a detector 24, collectively, the collection optics, for detecting radiation collected from the illuminated sample 18 which passes the second light restrictor. In addition, system 10 contains a controller 26 which can be coupled with the illumination and collection optics or parts thereof, for coordinating their positions so the illumination is directed to, and response is collected from a selected volume element, e.g., for aiming the probe to provide discrete depth sections or volume element sampling. This is specifically achieved by having field stops in the illuminating and collecting restrictors 14 and 22 conjugated to each other via the sampled volume element as will be further detailed below.

In operation, illuminator 12, restrictor 14, and directing optics 16 together illuminate a volume element in sample 18. Illuminator 12 generates radiation and directs it towards restrictor 14. Light restrictor 14 selectively transmits portions of the radiation on to the illuminating objective 16, which focuses, or images, the light restrictor field stop onto a volume element contained within sample 18.

Collector optics 20, restrictor 22, and detector 24 jointly operate to detect radiation emanating toward the collector optics from at least a portion of the illuminated volume element. Collector optics 20 form an image of the illuminated volume element contained in sample 18 on the field stop of the second light restrictor 22. The second restrictor 22 then selectively passes the radiation from the collector 20 on to detector 24. Detector 24, in turn, identifies characteristics of the electromagnetic radiation, such as its intensity at one or more spectral lines or regions of the spectrum.

The cooperative restrictions of the illumination and response collection provide spatial filtering of all responses outside of a discrete volume element, thus dramatically increasing the signal to background ratio of the detected signal from that volume element.

Controller 26 can sequentially adjust the positions of directing optics 16 and collector optics 20 to illuminate and detect a plurality of volume elements contained in sample 18, or it can adjust the positions of the light restrictor field stops to achieve the same effect. In another aspect of this invention, controller 26 scans the illumination beam and the detecting beam across a two dimensional area of sample 18. This is done by redirecting the beam axes of system 10, relative to sample 18, to various positions offset in a direction orthogonal to the axis of the beam of radiation illuminating a volume element within sample 18. Thus, controller 26 provides for movement or aiming of system 10 relative to sample 18 along three mutually orthogonal axes or independent directions.

Figure 2:
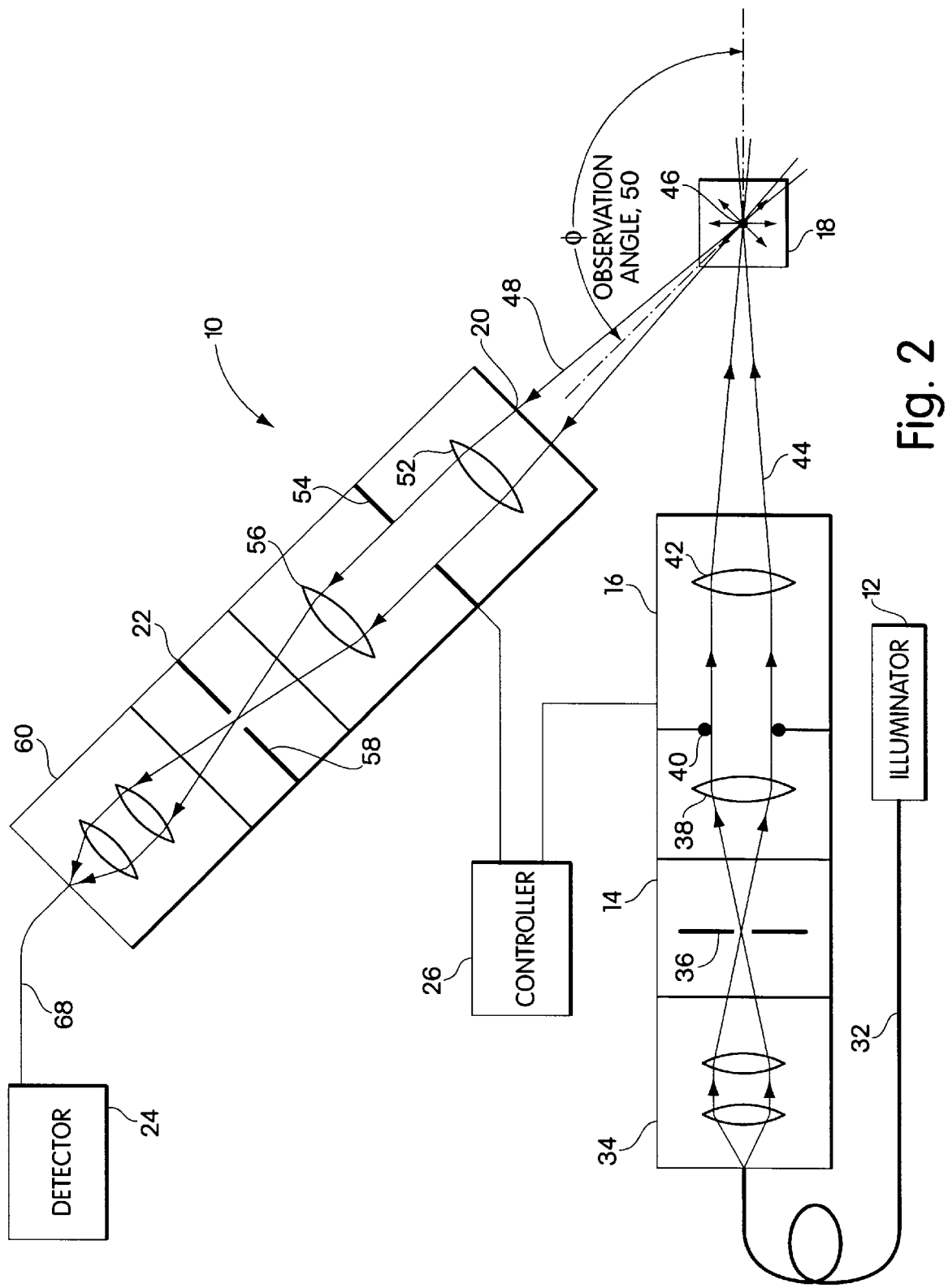
FIG. 2 shows a schematic representation of a volume probing system according to the present invention.

FIG. 2 illustrates representative physical elements implementing a system 10 according to the invention for probing a plurality of volume elements within a sample. The illustrated system 10 includes light source or illuminator 12, an illuminator coupler 32, illuminator coupling optics 34, first light restrictor 14, containing the first field stop 36, and imaging means, shown as an illumination objective 16 consisting of the lenses 38 and 42, the latter being the front assembly of the objective 16, and aperture stop 40 for illuminating a volume element 46 contained in sample 18 with an input radiation beam 44 derived from the first light restrictor. FIG. 2 further illustrates a collector 20, consisting of lenses 52 (objective front assembly) and 56, and aperture stop 54, a second light restrictor 22 containing a second field stop 58, detector coupling optics 60, detector coupler 68, and detector 24 for capturing and analyzing the return radiation 48 emanating from the volume element 46.

Illuminator coupler 32 in conjunction with illuminator coupling optics 34 provide a path for electromagnetic radiation to travel from illuminator 12 to the restrictor 14. Detector coupler 68 and detector coupling optics 60 provide a path for electromagnetic radiation to travel from the second light restrictor 22 to detector 24. Coupler 32 and coupler 68 can be either an optical fiber having a diameter ranging typically from 50 micrometers to 200 micrometers, or a wave guide. Generally, the optical fibers or wave guides are multi-mode, i.e. couplers 32 and 68 can transmit broadband electromagnetic signals. Illuminator coupling optics 34 and detector coupling optics 60 each typically contains a lens or similar element for realigning or matching the electromagnetic waves traveling between couplers 32 and 68, respectively and the other portions of the system. The lenses in the coupling optics 34 and 60 form a precisely aligned transition minimizing power loss as the electromagnetic radiation exits or enters couplers 32 and 68 respectively.

The illustrated first light restrictor 14 contains a field stop 36 which is intended to be representative of any restrictor used in optical systems to limit the field of view. Generally, reference to a "field stop" in this specification is intended to mean any opening having any shape, such as a circular, elliptical, square, slot-like or rectangular opening which limits the field of view. In addition, it is understood to include openings having a static shape and size as well as openings having an adjustable shape and size, such as a restrictable iris, and to include system elements having an aperture which are commonly utilized to perform the function of a field stop such as an optical fiber of defined effective cross-sectional area. In operation, field stop 36 selectively restricts light entering directing optics 16 by blocking light. Lens 38, as illustrated, collimates the light passing through the field stop 36. In one embodiment, the collimated rays of light in the first portion of the illumination assembly enable directing optics 16, which act as an illumination objective, to be shifted axially without requiring any further adjustment of the position of light restrictor 14. Such adjustments, which are under the control of controller 26, allow for changing the focal point of the beam 44 in the axial direction to illuminate a selected discrete volume element along the beam axis.

Objective optics 16 can include a first aperture stop 40 to limit the aperture of the objective lens in addition to the opening defined by the edge of the lens assembly 38 and 42 for imaging the resultant beam into a defined probe volume 46 in sample 18. If provided, such an aperture stop 40 serves to further restrict or define the cross-sectional size of the electromagnetic radiation beam projected by lens 42 to illuminate sample 18. Lens 42 generally operates by causing a beam of radiation 44 to converge to a narrow image of the field stop 36 at a focal region in sample 18. The volume in sample 18 where the beam of radiation 44 comes to a focus includes the probed volume element 46, as described in more detail in FIG. 3.

Light restrictor 14 and the focusing power of directing optics 16 cause the intensity of input radiation 44 to be strongly peaked at the focal region of the objective optics 16 at which the opening of restrictor 14 is imaged so that the intensity of radiation 44 falls off both transversely and along the line of sight away from the aforementioned focal region in sample 18.

When input radiation 44 illuminates the probed volume element 46, the radiation interacts with materials within the sample volume limited by the field stop 36. This interaction generally results in a secondary beam of light emanating from the illuminated sample in all directions ($4\pi$ steradians). This secondary beam, the response of the sample to the impinging radiation, can include reflection off material within the sample volume, scattering, and absorption (observed as lack of response in specific parts of the spectrum), as well as unique fluorescent emissions of light. A portion of this optical response from the sample volume, the collected radiation 48, reaches the collector and is picked up and coupled to the detector 24.

The collector assembly 20 can include a front objective lens 52, a second aperture stop 54, and a relay lens 56 which together gather the radiated energy 48 emanating from the probed volume 46 and image the largest cross section of said volume element perpendicular to the beam onto the field stop 58. In one embodiment, lens 52 has a focal length equal to its distance from said cross section and thus can gather the collected radiation 48 and redirect the radiation 48 in a collimated manner. The aperture stop 54 selectively passes a radiated beam of defined size from the light gathering objective lens 52, and a second lens 56 images the aforementioned cross section of the volume element 46 into the second light restrictor 22.

The illustrated second light restrictor 22 contains a field stop 58. Field stop 58 is intended to be representative of any opening used in optical systems common in the art. In operation, collecting element 20 images on field stop 58 the volume element 46, or to be more accurate, the largest cross section of said volume element perpendicular to the collection optics' axis. Therefore, field stops 58 and 36 are conjugated to each other via the volume element 46. The light passing through the field stop 58 travels through coupling optics 60 and detector coupler 68 to reach detector 24. The spatial filtering of the illumination beam to have the highest irradiance in the sample volume element 46, coupled with the spatial filtering of light emanating from the volume element 46, combine to strongly discriminate against reception of light emanating from regions outside the volume element 46.

Figure 3A:
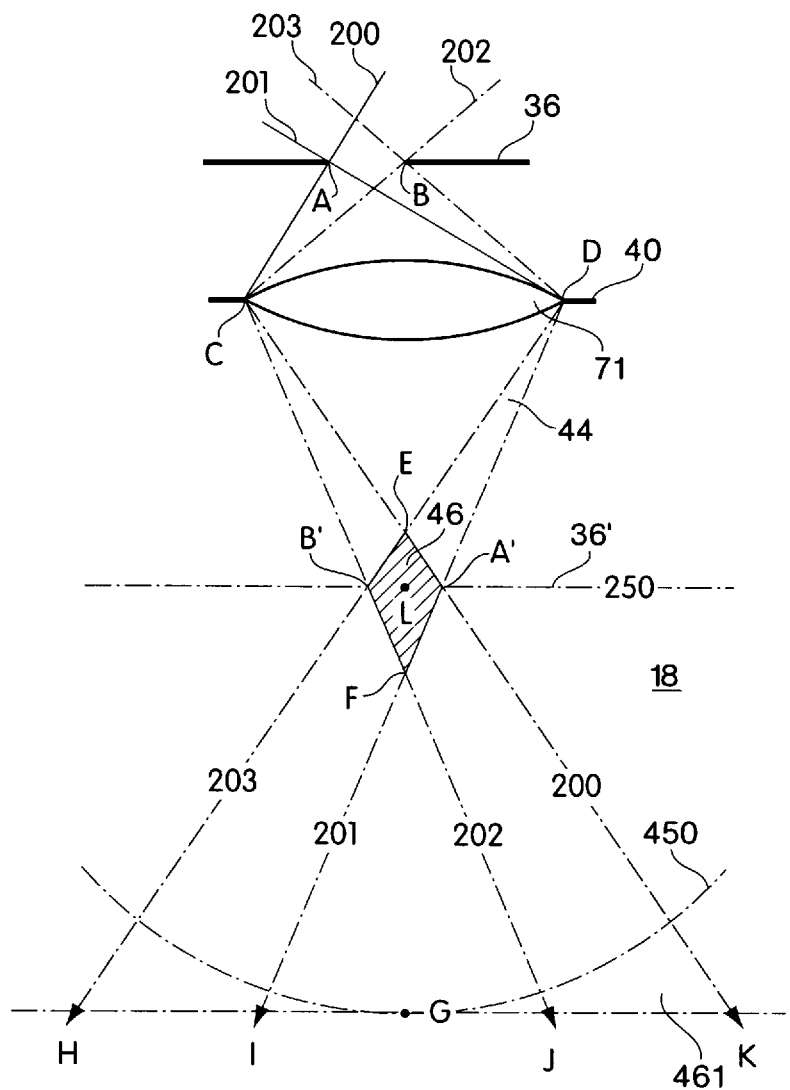
FIGS. 3A, 3B and 3C illustrate illumination and light collection portions of a system, and their alignment to define observable volume elements, respectively.
Figure 3B:
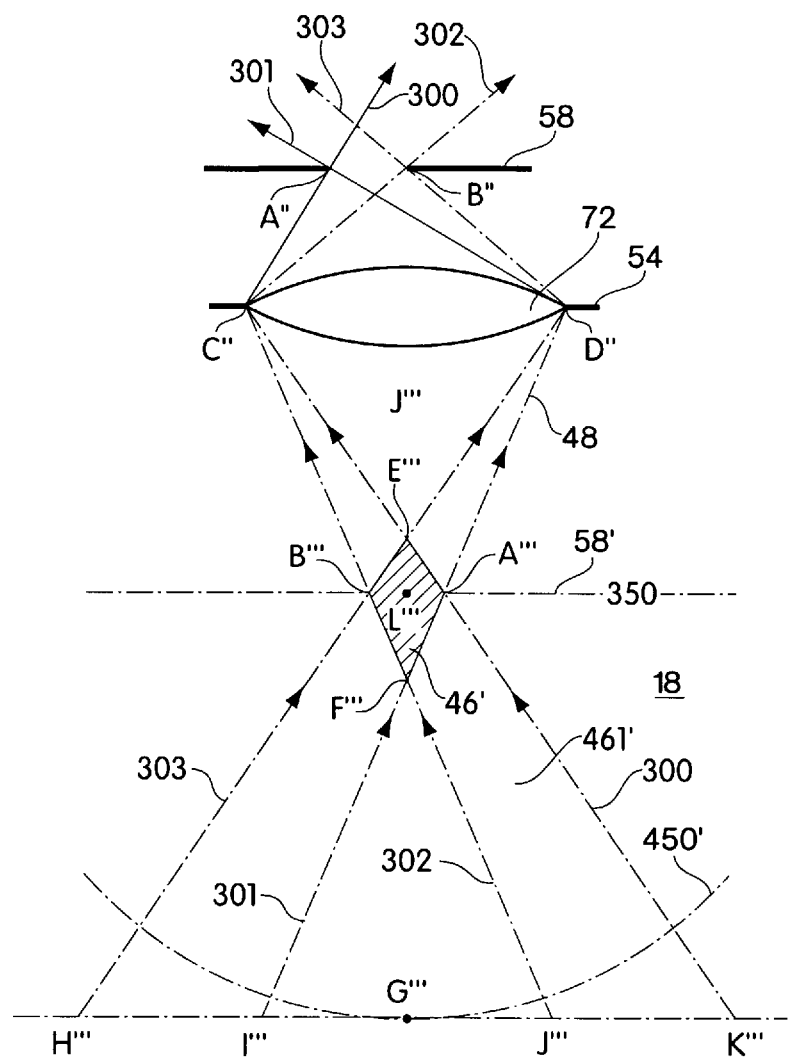
Figure 3C:
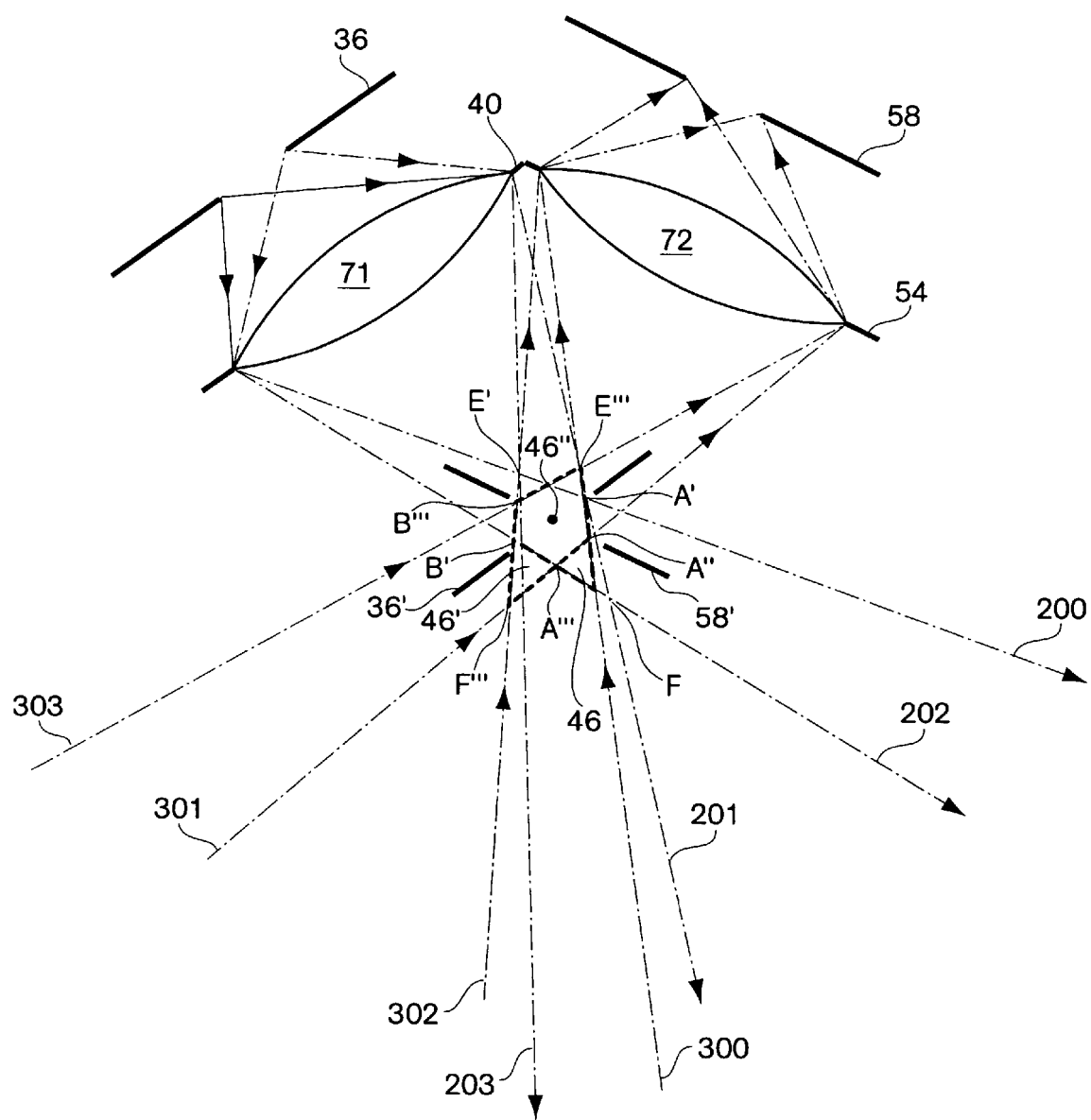

The effect of mutual conjugation of the field stops in restricting the volume element from which emanated radiation is detected will be better understood by examining FIGS. 3A, 3B, and 3C, which represent cross sections of the optical system.

FIG. 3A illustrates the illumination subsystem, where the illuminating field stop 36 is imaged by optical element 71 (representative of the objective 16 of FIG. 2). Marginal rays 200 and 201 originating in the illuminator 12 (FIG. 2) propagate from point A of the field stop 36, and marginal rays 202 and 203 propagate from opposite point B. The marginal rays 200 and 202 pass through the margin C of the aperture stop 40; whereas marginal rays 201 and 203 pass through the opposite margin of the aperture stop D. Rays 200 and 201 converge in the image plane 250 at A', the image of point A. Similarly, rays 201 and 203 converge in the image plane at point B', the image of B. A' and B' are extremities of the cross section of the image 36' of field stop 36. If field stop 36 is a circular aperture, points A' and B' lie on opposite ends of a diameter of its circular image 36'. Marginal rays 200, 201, 202, and 203 then continue propagating into the specimen 18 as shown in FIG. 3A.

In the geometric optics approximation to non diffraction limited imaging, marginal rays 200, 201, 202. and 203 are geometric boundaries of the input radiation 44. In the absence of scattering within the specimen 18, all input radiation 44 is contained within an illuminated volume 461 bounded by points H, B', C, D, A', K. All illuminating radiation propagating through interior points of the field stop 36, which also propagates through the aperture stop 40, will pass through the volume element 46 whose cross section is bounded by points A', F, B', and E. When field stop 36 is circular, volume element 46 is biconical and formed of two right circular cones with apices at E and F and with common base 36'. As will be made more clear in FIG. 3B, volume element 46 is the only volume element in specimen 18 in which radiation 44 is unvignetted.

The irradiance is maximum at the image 36' and falls rapidly outside the volume element 46. For clarity, in FIG. 3A, the relative size of the field stop 36 and its image 36' are shown greatly exaggerated compared to the diameter of the aperture stop 40 or to the working distance from the objective 71 to the image plane 250. Thus, the irradiance inside the illuminated volume 461 and outside the volume element 46 falls approximately as the square of the distance from the center L of the image of the field stop 36', for example at point G.

The radiation 44 interacts with the specimen 18 which, as a result, is made to emanate radiation. The nature of the emanated radiation depends on the nature of the interaction and may include emanation into the entire sphere ($4\pi$ steradians) surrounding any source point G in the illuminated volume 461, for example, when the emanated radiation is fluorescence, or may be a more directional emanation such as a forward dispersion or partially absorbed beam, or a backscattered beam. The strength of this emanation from any source point G will be proportional to the strength of the radiation 44 at that point.

For clarity of illustration first consider the collection subsystem separately from the illumination subsystem. Because of the inherent reversibility of fundamental optical laws, any argument properly applied to the distribution efficiency of the illumination subsystem can be shown to apply to the collection efficiency of the conjugated collector subsystem. This reversibility is illustrated in FIG. 3B showing the collection subsystem. Volume 461' contains sources which emanate radiation which can be collected and then detected by the detector 24 (FIG. 2), and, when illumination and collection are considered together, will correspond, at least in part, to the illuminated volume 461 of FIG. 3A.

As illustrated in FIG. 3B, radiation emanating from a point in the volume 461' will reach the detector 24 only if that radiation propagates though both the collector aperture stop 54 and the collector field stop 58. The radiation emanated from the specimen 18 which can reach the detector is included in the radiation 48. In non diffraction limited imaging, marginal rays 300, 301, 302. and 303 are geometric boundaries of the collectible radiation 48. In the absence of scattering within the specimen 18, all collectible radiation 48 emanates from, and is contained within, the volume 461' bounded by points H''', B''', C'', D'', A''', K'''. All emanated radiation 48 propagating through interior points of the field stop 58, which also propagates through the aperture stop 54, will pass, or be projectable, through the volume element 46' whose cross section is bounded by points A''', F''', B''', and E'''. When field stop 58 is circular, volume element 46' is biconical and formed of two right circular cones with apices at E''' and F''' and with common base 58'.

Any ray of radiation 48 which passes through the field stop 58 must also propagate through the image 58', if it originates in 18 below the image 58' (on the far side of plane 350 from objective 72), for example at point G'''. Furthermore, any ray of 48 which passes through field stop 58 must also propagate so that it can be projected backwards through the image 58', if it originates above image 58' (between plane 350 and the objective 72). Firstly, all radiation which can be collected must be directed into the collection aperture of the objective 72, that is, lie within the volume 461' and be directed toward the aperture stop 54; secondly, all radiation that achieves the detector 24 must propagate through the field stop 58. This second condition causes the collection efficiency of the collection subsystem to fall off approximately as the square of the distance of a source point, for example, G''' from the center L''' of the image 58' of the detector field stop.

For clarity, in FIG. 3B, the relative size of the field stop 58 and its image 58' are shown greatly exaggerated compared to the diameter of the aperture stop 54 or to the working distance from the objective 72 to the image plane 350. In actual practice, the angle C"F'"D" closely approximates the angle C"E'"D", and, in calculations of efficiency or irradiance, either can be replaced by the angle C"L'"D" with small loss in accuracy. The function $\sin(\frac{1}{2}\angle C"L'"D")$ is the working numerical aperture (NA) of the objective 72 and defines the nominal collection angle of the objective for light falling on the aperture stop. From FIG. 3B it can be seen that, for source points in 461' but outside the volume element 46' and significantly below the plane 350, for example the source point G''', the solid angle subtended by the image of the field stop 58' from G''' is smaller than the solid angle subtended by the aperture stop from the center L''' of the image 58'. Thus, rays emitted from G''' may lie within the solid angle collected by the objective 72, but will not propagate through the field stop 58, because no such rays can propagate through the field stop without first passing through its image 58'. Therefore, the collection efficiency for such points falls as the ratio of the solid angles so subtended, which can be expressed as falling as the square of the distance of a source point, for example, G''', from the center of the image 58'. For rays emitted into 48 from source points in the sample 18 outside volume element 46' and between the plane 350 and the objective 72, the image 58' subtends a smaller solid angle than the aperture stop; thus for these source points, the area of the aperture stop through which rays may propagate and pass the field stop is reduced, and the collection efficiency falls in the same manner.

For source points within the volume element 46', any ray emitted into the actual collection angle of the objective 72 may propagate to the detector 24. Thus, volume element 46' is the only volume element of specimen 18 from which emanating radiation 46 is unvignetted.

Thus, vignette operates in applicant's non diffraction limited conjugated optical system to limit the volume element from which significant signal is detected.

FIG. 3C shows the volume element 46" defined by the conjugated illumination and collection optics when the observation angle Ø (50 in FIG. 2) is not 180°. As can be seen from FIG. 3C, the depth discrimination is generally improved and the signal is only slightly weaker than when a common field stop and common objective assembly are used, because of the substantial but incomplete overlap of volume elements 46 of FIG. 3A and 46' of FIG. 3B. The shared volume element 46" which consists of the intersection of volume elements 46 and 46' is the volume element-through which the field stops are conjugated. In general, with the field stops centered as shown and their images crossing only at a point, the peaks of the unvignetted biconical volume elements are clipped to provide a smaller element, of lesser top-to-bottom depth, shaped like the intersection of conic sections, from which the optical response is selectively enhanced. The illumination and collection systems may also be shifted translationally, so that this crossed intersection of field stop images assumes a less symmetrical shape- e.g., a sliver, wedge or sheet—which is even more localized and may be shaped like or aligned obliquely with a feature of the sample being observed. In that case although the total signal may be greatly reduced, the proportion of detected signal emanating from the sample may be increased, enhancing its useful information content or its correlatability to a characteristic of interest.

System 10 uses the conjugate stops 36 and 58 to limit the fields of view, both transversely and in depth, within sample 18, defining probe volumes elements tailored to the intended characterization task of the system. A person trained in the art would note that while the field stops 36 and 58 are conjugate to each other via volume element 46", as shown in FIG. 3C, the two field stops are not confocal, in that the respective images of the two field stops, the cross sections 36' and 58' respectively in FIG. 3C, do not overlap but have only a common line, the intersection of the cross sections 36' and 58'. In general, the optical paths, the field stop shape and position, and the objective elements may be aligned so that they define volume elements which are both localized and oriented. For example, shapes such as slivers, wedges, meniscii, conic sections and the like may be realized by the intersection of illumination and collection regions.

A person trained in the art will also appreciate that rather than full conjugation of the two field stops, the invention also includes other non imaging volume microprobe systems, wherein the detection volume is defined by sheared conjugation, namely the partial overlap of the field stop images, and thus the partial overlap of the two biconical structures discussed herein. One preferred embodiment of such systems employs the illuminating and collection optics parallel to each other and the objectives slightly displaced or provided with a wedge to form a common image overlap region in the specimen of the two field stops, which is offset from the respective optical axis of both assemblies.

As illustrated in FIG. 3C, in any of these configurations the interaction of the impinging beam 44 with matter of volume element 46", which is the volume common to both light paths cited herein, is thus spatially filtered twice and the detected light from this volume may be expected to have an amplitude that drops off as the product of the illumination and the collection distributions. Much lower levels of light illuminate out of focus volume elements in sample 18, so that advantageously, the non-selected elements do not significantly mask the image of the more brightly illuminated focal region, or probe volume 46. Furthermore, from the low level light that does reach out of focus material, not inside a selected volume element, only a very small portion reaches the collecting optics. In essence, the contribution to the detected signal of light originating outside the common volume element 46" decreases as the fourth power of the distance from the common center of the biconical structures cited herein. This results in a many-fold enhancement of the return signal which may be collected using apparatus of the present invention from the selected volume element, relative to the signal collected from outside that volume element.

As for size, by way of example, for probing a biological tissue sample having a fundamental microstructure consisting of cells with a characteristic dimensions of one to twenty micrometers, and a clinical macrostructure which may extend across layers or growth processes ten to a thousand times larger, a probe instrument may have its illumination field stop defining the illumination volume selected to be tens to hundreds of micrometers in size; the collection field stop may also be tens to hundreds of micrometers in size. In typical embodiments, contemplated by applicant, the illumination and collection field stops are between twenty-five micrometers and five hundred micrometers, and the magnification of the objective is between one tenth and one. The characteristic dimensions d of the field stops in typical embodiments are set by these requirements.

For practical optical systems, this requires the use of large field stops.

The image of a point-like object formed by a well-corrected objective lens is not point-like. It is generally complex, consisting of a brightly illuminated central spot, which encompasses more than one-half of the power in the image, with the remaining power distributed over the image in accordance with the shape of the aperture stop and in accordance with the amplitude and phase distribution of the light incident on the aperture stop. Evaluation of Maxwell's Equations in the appropriate approximation show that the central spot has dimension $d'=k\lambda/NA$, where $\lambda$ is the wavelength of monochromatic incident light, NA is the image-side working numerical aperture of the objective, and k is a coefficient of order unity. For example, for the most common case in practical optics, a plane or spherical wave incident on a circularly symmetric well-corrected objective, the image is the Airy pattern familiar to one skilled in the art, and the diameter across the first nulls surrounding the central maximum is $d'\approx 1.2\lambda/NA$; approximately 84% of the power in the image is contained within that diameter.

As another example common in practical optics, in the case where the incident light is a lowest order $TEM_{00}$ laser mode, the irradiance at the image is distributed as a Gaussian function with the conventionally defined diffraction spot diameter $d'\approx 0.64\lambda/NA$; at that diameter the image irradiance is approximately 13.5% of the maximum irradiance at the center of the diffraction pattern and the power encompassed is approximately 87% of the total power in the image. Accordingly, the field stops contemplated for use in the present invention have diameter $d>k\lambda/NA$ where k is the constant of proportionality appropriate to the aperture stop and incident light employed. For any practical combination of objective lens, aperture stop, and illumination, it is sufficient for $d>2\lambda/NA$, and in practice usually $d>>\lambda/NA$.

Neither is the image of a large object formed by a well-corrected objective the perfect replica predicted by geometric optics. Careful examination of the edges of the geometric image will reveal diffraction effects, but these effects are negligible except for images whose size approximates the diffraction spot, because substantially no optical power is found outside the geometrical image. Thus the distribution of optical power in the image plane can be used as a criterion of whether an object, like a field stop, is so small that diffraction effects dominate the optical performances of its associated objective. One such criterion is, for example, that 95% of the optical power from an object which reaches the image surface be encompassed by the geometrical image of that object.

In the embodiment of FIG. 2, of the instant invention, the selection of the volume element 46, along the optical axis is achieved by the synchronous axial movement of the objectives' front assemblies (42 and 52 respectively). This, since we chose to have the front assembly of the objectives at a distance equal their respective focal point from the selected volume element 46. It should be understood, however, that when a new volume element need be selected, either the sample is moved relative to the two (fixed) optical assemblies or one of the optical assemblies is moved relative to other to keep the selected volume element as the conjugating point for the two field stops.

Other means to obtain volume selection along the optical axis, z, of the illumination system, utilizing other movements of elements are also contemplated, including the movement of the field stop, or movement of other optical elements that modify the imaging distance of the objective of the illumination system. However, any movement in one of the two optical assemblies is to be compensated by a related movement in the other, e.g., in the collection optical assembly to assure that conjugation or sheared conjugation of the two field stops is achieved via the selected volume element 46.

Figure 4:
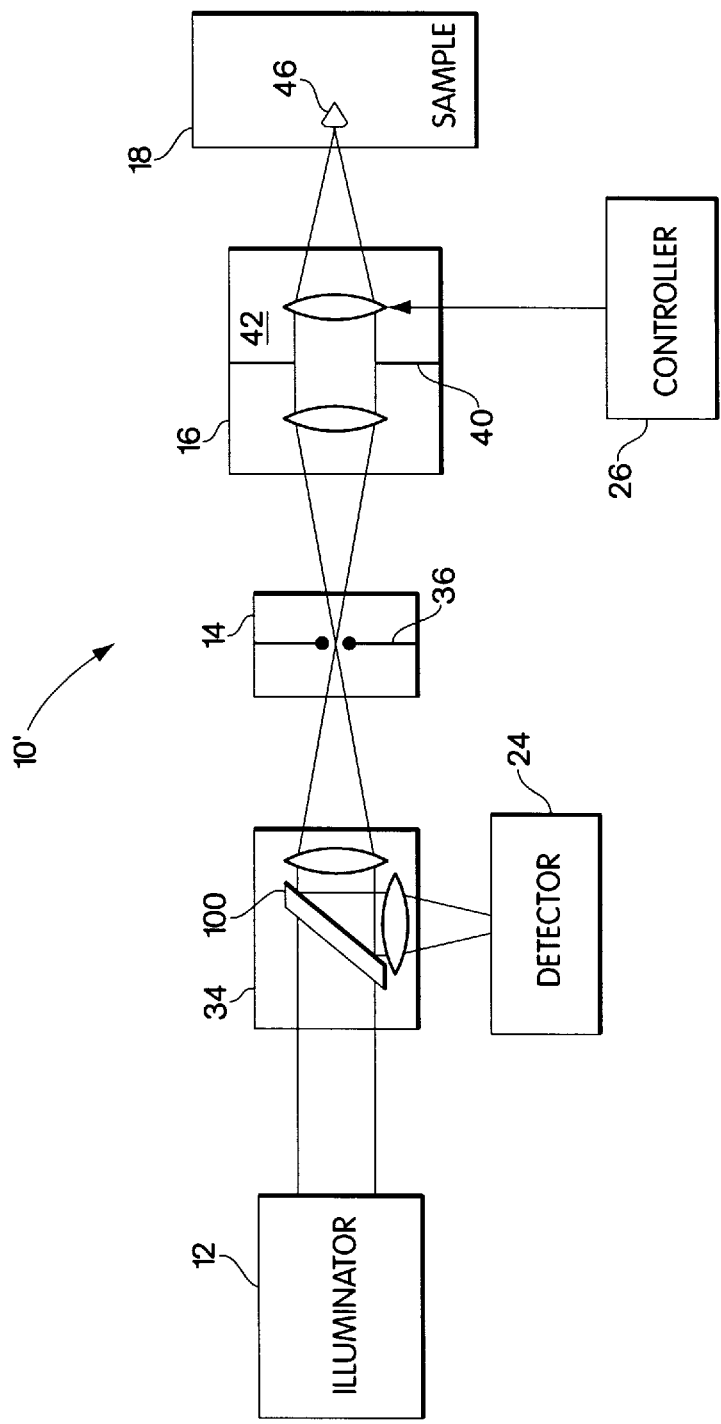
FIG. 4 shows a schematic representation of another embodiment of a volume probing system according to the invention.

FIG. 4 shows a modified system 10' which reduces the need for coupling motive assemblies in a non imaging volume microprobe, wherein a common objective assembly is employed to illuminate a specimen and to collect light along the same axis or path. System 10' has an illuminator 12, coupling optics 34, beam splitter 100, first light restrictor 14, objective 16, detector 24, and a controller 26 configured for sampling volume elements at different depths by shifting the front objective optics elements 42. The beam splitter 100 is interposed between the front and back elements of coupling optics 34 and reflects light entering from the direction of the light restrictor 14, but passes light arriving from the direction of the illuminator 12. The reflected light from beam splitter 100 is directed towards the detector 24.

In operation, illuminator 12 generates a beam of radiation which travels through coupling assembly 34 and the beam splitter 100 towards the light restrictor 14. Light restrictor 14 selectively transmits the beam of radiation which has passed through a field stop 36 to the objective 16. Objective optics 16 form an image in the sample 18 of the field stop opening 36. Light reflected or emitted from sample 18 is then collected by the objective optics 16 and is focused back through the same field stop opening 36 in the light restrictor 14, which thus selectively passes only a portion of the radiation from the sample 18 that reaches the objective. The portion passed consists predominantly or essentially of responses from the volume element 46. The selectively transmitted beam continues towards beam splitter 100. Beam splitter 100 redirects at least a portion of the selectively transmitted beam towards the detector 24 for recording analysis and characterization. As in the embodiment of FIG. 2, the illumination source and light restrictor form a larger than-diffraction-limited illumination spot of localized intensity in the sample.

Figure 4A:
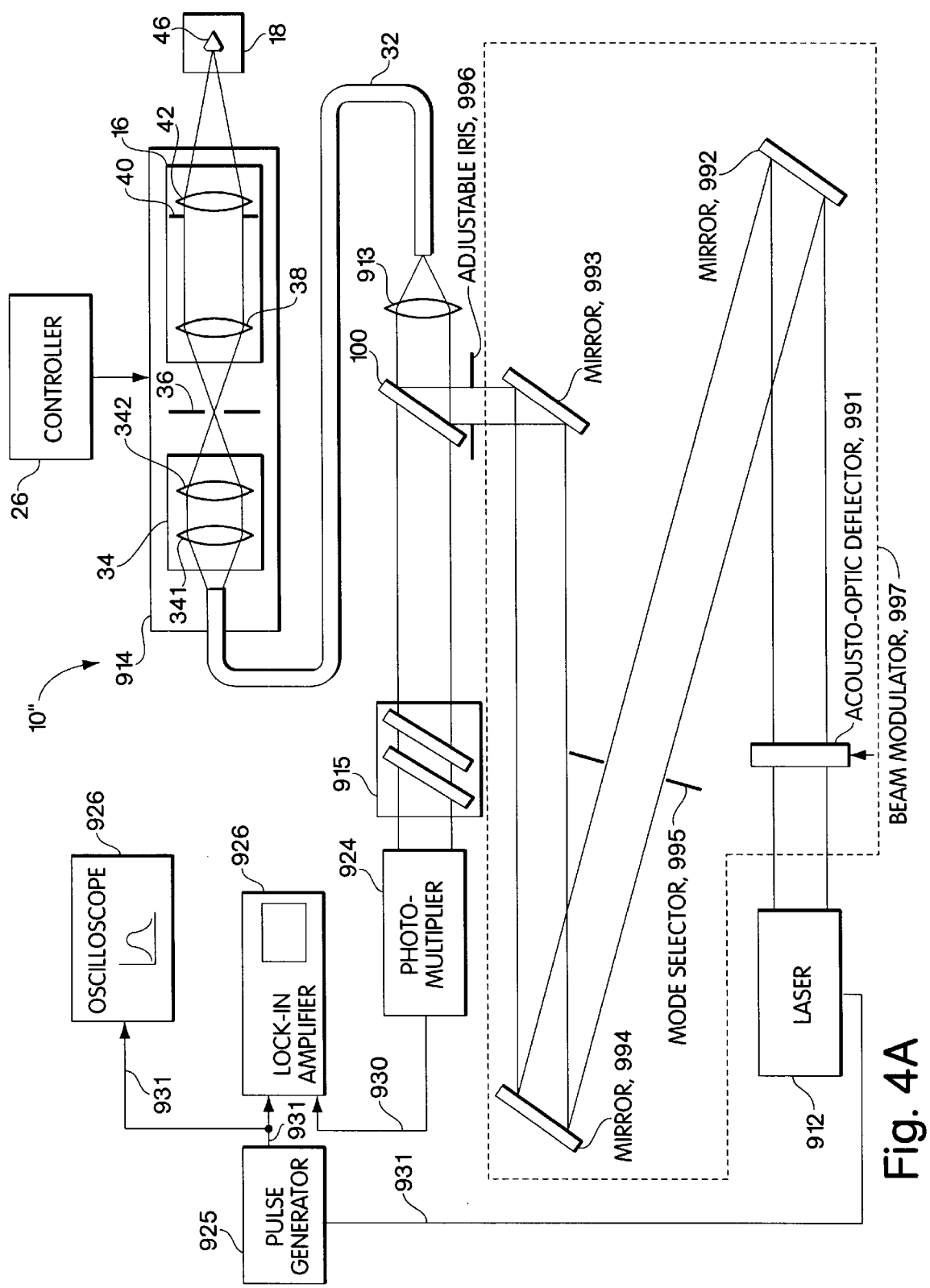
FIG. 4A is a diagram of a practical system implementing the schematic of FIG. 4.

FIG. 4A shows another embodiment 10" wherein a common objective assembly is employed to illuminate a specimen and collect light along the same path. System 10" has as illuminator a laser, for example a Melles Griot 05-LHP-121-111 with linearly polarized output at 633 nm wavelength, a beam modulator assembly 997 employed to pulse the laser output to permit synchronous detection for signal enhancement, a polarization sensitive dichroic beam splitter 100, for example one manufactured by the Reynard Corporation for use with 633 nm radiation at 45 degrees incidence, disposed so that it reflects more than 90% of the incident polarized laser radiation, a coupling lens 913, for example Melles Griot LAO011 with focal length of 20 mm, which couples the laser radiation into illumination coupler 32 while matching the acceptance numerical aperture of the coupler 32. This coupler consists of an optical fiber, for example a two meter length of CeramOptic UV200/220A12 with 200 micron core and numerical aperture (NA) of 0.12 enclosed in a nylon jacket and terminated with Augat SMC connectors, an optical head comprised of coupling optics assembly 34, field stop 36, for example a National Aperture stainless steel field stop with a 100 micron laser cut aperture in a PA-3 Adapter, and an objective assembly 16, which collectively serve to illuminate the sample 18. The sample 18 may be a phantom used to calibrate the performance of the system 10", consisting for example, of scattering elements and a fluorescent dye, Nile blue, dispersed in a transparent medium, or, for example, it may be comprised of scattering elements dispersed in a transparent medium under the surface of which is inserted a thread soaked in a dye such as Nile blue to mimic a small cancer, or it may be comprised of natural tissue like chicken breast into which is inserted a thread soaked in a drug normally used for cancer therapy, so as to mimic the absorbency and emission characteristics of a small tumor treated with such a drug; alternatively, the sample may be such a tumor so treated. The illuminated Nile blue emits fluorescence concentrated at wavelengths between 670 nm and 780 nm. The optical head collects the fluorescence generated in volume element 46 of sample 18 and couples it into illumination coupler 32 which emits into the acceptance numerical aperture of the coupling lens 913 which, in turn collimates the collected radiation and passes it to the dichroic beam splitter 100. Beam splitter 100 transmits more than 90% of the fluorescence at wavelengths greater than 670 nm. The transmitted fluorescence passes through a set of optical filters 915, for example Schott R68 glass, which transmit less than one part in $10^4$ of scattered 633 nm illumination but transmit more than half of the fluorescence to detector photomultiplier 924, which may be, for example, an Hamamatsu R928. The electrical output 930 of the photomultiplier 924 is passed to a lock-in amplifier 926, for example a Princeton Applied Research SR530 amplifier. The electrical output 931 of the pulse generator 925, (a Hewlett Packard 8003A) is adjusted to oscillate, for example, at approximately 850 Hertz to control the beam modulator assembly and to synchronize the modulator assembly and lock-in amplifier. The lock-in amplifier processes the electrical output 930 of the photomultiplier 924 and displays its average strength on a display and also passes a signal proportional to the average strength to an oscilloscope 926, for example a Tektronix 475. The displayed signal strength is proportional to the fluorescence emitted from the volume element 46 being measured. A controller 26 is employed to move the optical head 914 in three orthogonal directions so that the fluorescence of different volume elements may be measured.

Specifically, the modulator assembly comprises an acoustic optic deflector, for example an Isomet 1201E with 221A-2-39 driver, which generates deflected first and higher order beams when pulsed by the pulse generator 925 and which generates an undeflected zeroth order beam when the pulse generator output is off. The output beam passes from the laser 912 through the acousto optic deflector 991 to a turning mirror 992 which directs the beam to a mode selector 995. The mode selector 995 might be, for example approximately 800 mm distant from the deflector 991, so that the deflected beams impinge the mode selector well separated from the impingement point of the undeflected zeroth order beam. The mode selector contains an aperture which is large enough, for example approximately one millimeter in diameter, that the first order beam can pass, whereas the body of the mode selector intercepts and blocks transmission of the other modes. The first order comprises the laser illumination which impinges on a second turning mirror 994 and which is directed onto the beam splitter 100 through an adjustable iris 996 which is set, for example, to approximately 3.5 mm in aperture. The adjustable iris acts to remove any other residual deflector modes which leak through the mode selector 995 and to remove any portions of the incident laser beam other than the lowest order $TEM_{oo}$ Gaussian mode which predominates in the output of the laser illuminator 912. This final cleaning of the illumination beam reduces scattering by the following optical elements of illumination into the optical path directed toward the photomultiplier. Thus the laser illumination which enters the optical head 914, is a cleaned up beam pulsed at the pulse frequency of the pulse generator 925.

The optical head coupler includes front and back elements 341 and 342, respectively, for example a pair of Edmund Scientific M6387 achromats with focal length 17 mm. Subassembly 34 matches the numerical aperture of the output of the illumination coupler fiber 32, and directs the illumination through the field stop 36 which may be, for example a circular aperture of diameter 100 microns which selectively passes the incident illumination with an efficiency of about thirty percent to the back element 38 of the objective assembly. Element 38, for example a Melles Griot 01LAO 028/078 with focal length of approximately 31.5 mm, is selected to maximize efficiency of coupling through the aperture stop 40 which is typically in the range 8 to 8.5 mm in diameter and integral to front element 42. Front element 42 is one of a set of microscope objectives chosen so that their magnification causes the image of the field stop to assume a desired diameter. Front element 42 may be, for example an American Optical Corp. 44X objective with focal length of approximately 4 mm and NA of 0.66, an infinity-corrected American Optical 20X PlanAchromat objective with focal length of approximately 8.5 mm and NA of 0.5, or an infinity-corrected Optics for Research 10X objective with focal length of approximately 20.3 mm and NA of 0.2 with long working distance of approximately 12 mm. These objectives were used to perform the measurements shown in FIG. 4B which verify the predicted performance of the system 10".

Figure 4B:
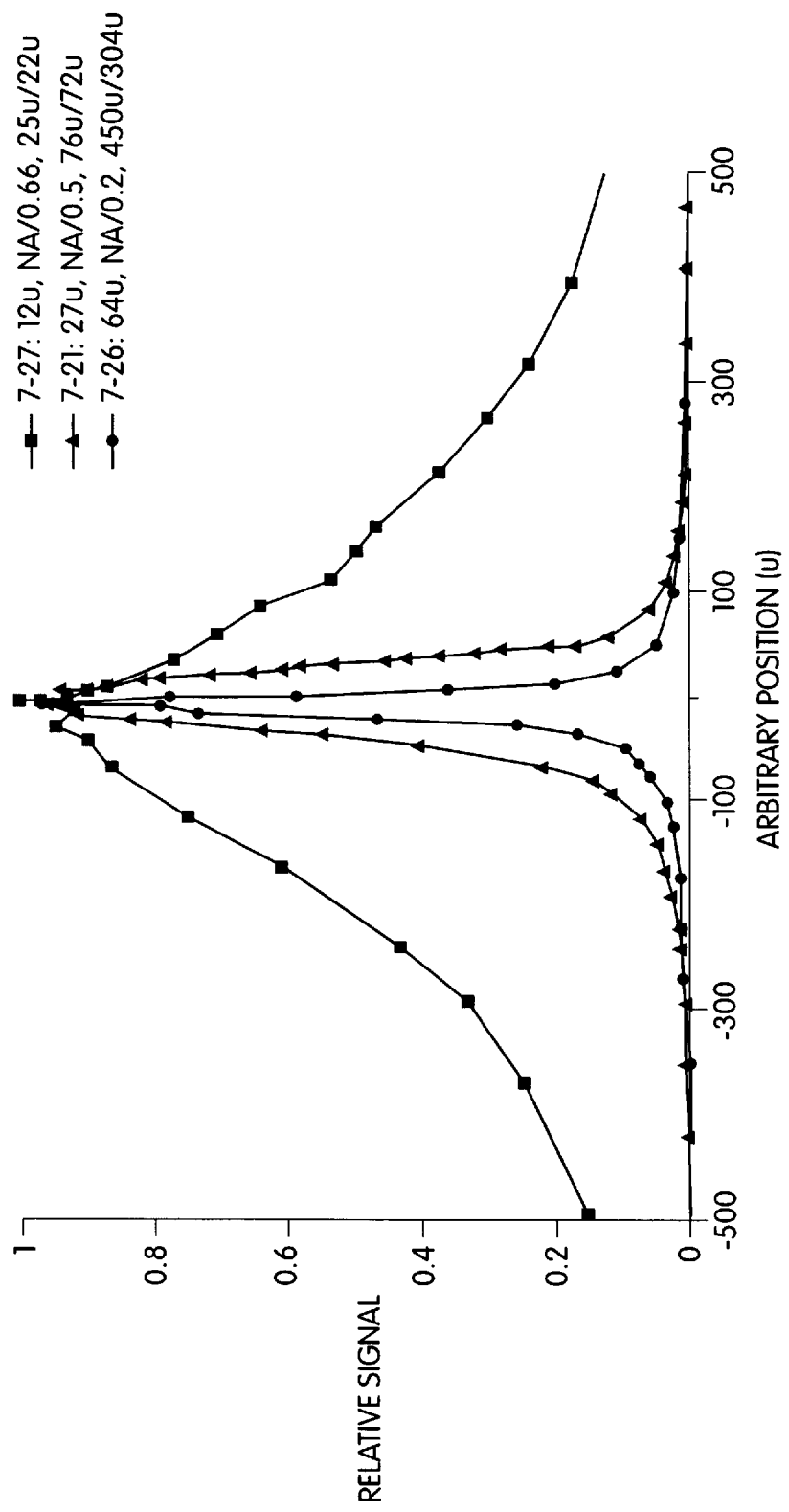
FIGS. 4B and 4C are graphs of light collected using the system of FIG. 4A.
Figure 4C:
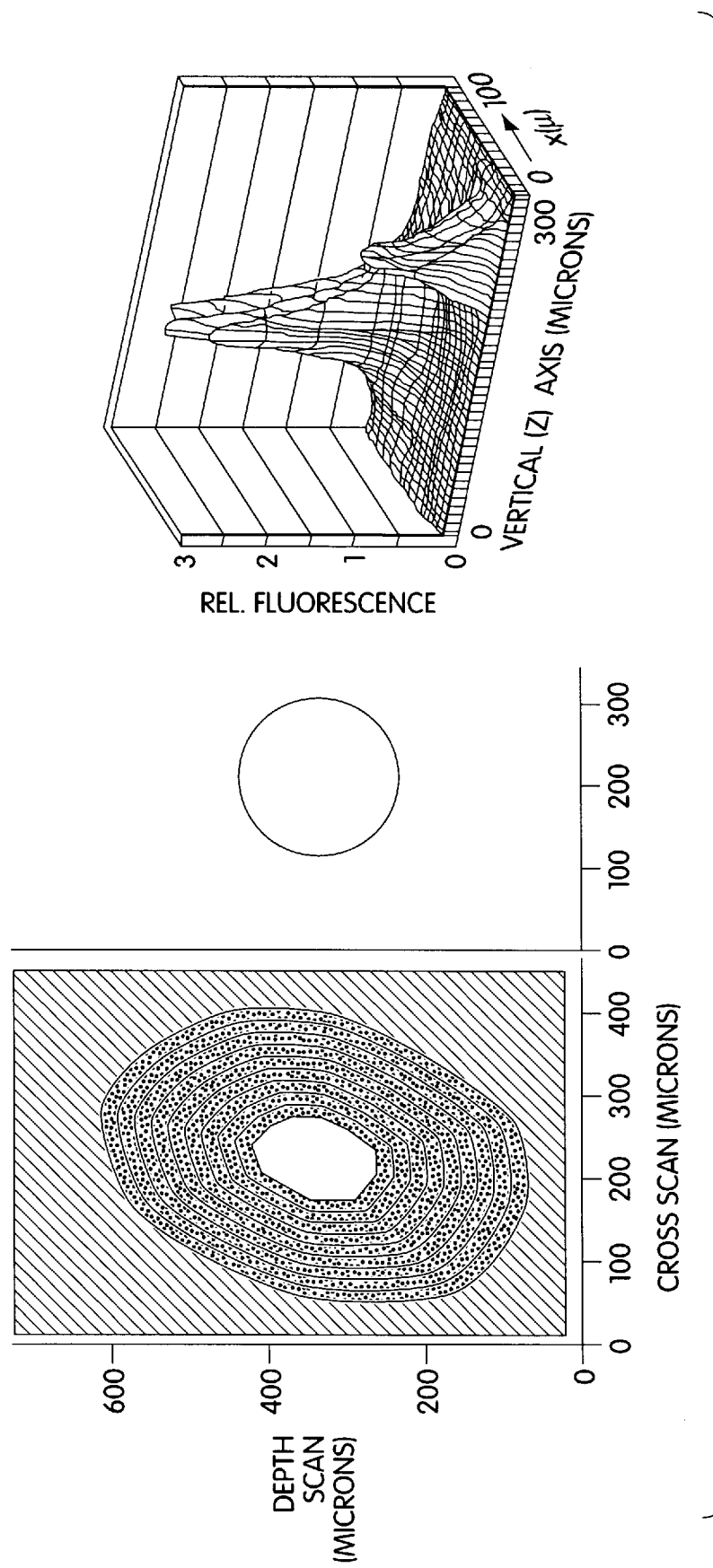

FIGS. 4B and 4C show measurements made with a practical working system of the embodiment of FIG. 4A.

In the embodiment of FIGS. 4 and 4A, the collecting and illuminating subsystems are congruent and several elements of FIGS. 3A and 3B are physically realized by the same elements; specifically the objectives 71 and 72, the aperture stops 40 and 54, and the field stops 36 and 58 are physically realized by the same hardware. In these embodiments, the field stops 36 and 58 are automatically conjugated through their common images 36' and 58' (FIGS. 3A and 3B) which are also common, as are the unvignetted illuminated and source volume elements 46 and 46' of FIGS. 3A and 3B. In this embodiment, the illumination efficiency and collection efficiency are highest at the common field stop image and, relative to distant points, for example G in FIG. 3A or G'" in FIG. 3B, remain high in volume element 46. Similarly the collection efficiency is high in volume element 46, which is identical to volume 46'. Overall efficiency of illumination and collection for a source point in 460, which is identical to 461 (FIGS. 3A and 3B), for example G, drops approximately as the product of the two (illumination and collection) efficiencies times a function relating the magnitude of emanation to that of illumination, i.e., approximately as the fourth power of distance from the center of the image 36' which is identical to image 58'. For points not on the optical axis, it can be shown that the drop off is even faster. Aside from losses in the specimen, a factor which does not materially affect the above reasoning, were it not for the limitation imposed by the collection field stop 58 the total flux of collected radiation 44 emanating from out of focus volume elements disposed along sphere 450 (450') could contribute approximately as much background signal to the radiation detected by the detector 24 as does the volume element 46 (46'), because the area of sphere 450' inside the illuminated and emanating volume 461 (461') increases approximately as the square of its distance from the image 36' (58'). However, in applicant's system, because of the collection field stop 58, the collection efficiency drop off is fast enough to ensure that the integrated background from all volume elements of 461' does not overwhelm the signal collected from the focal region, and specifically from the unvignetted volume element and its near neighborhood.

The full width half power depth discrimination of the non imaging volume microprobe system, δ, is approximately δ≈1.4d"/NA where d" is the diameter of the detector field stop image 58' and NA is the image-side working numerical aperture of the objective 72, and is thus determined solely by the geometry of the optical configuration. By contrast, in confocal microscopy, where diffraction dominated mechanisms control the illumination and collection efficiencies, the depth resolution Δ depends on the nature of the interaction of the incident light with the medium. For example, T. Wilson in Handbook of Biological Confocal Microscopy, J. B. Pawley, Ed., Chapter 11, 113–126, Plenum Press, New York, 1990 shows that for fluorescence confocal microscopy, Δ≈2.8λ/NA², where λ is the wavelength of monochromatic illuminating radiation, whereas Δ≈1.4λ/NA², when the incident and emanated light are coherent.

FIG. 4C shows two typical two dimensional scans of artifacts similar to a small photosensitizer-rich tumor using the apparatus of FIG. 4A. The first specimen was a 200μ thread (Talon-American Sewing Bee mercerized cotton #50) saturated in Nile blue, dried, and then coated with a thin layer of polymer (Duco cement) to prevent diffusion of the dye into the host tissue. The suture was then inserted 500–800μ below the surface in chicken breast. Excitation was at 633 nm and fluorescence was observed at wavelengths >670 nm. Depth resolution was ≈76μ and cross-scan resolution was ≈25μ; the suture is clearly resolved. Minimal data processing was used; for ease in establishing isointensity curves, the raw data was fitted with a sixth degree polynomial and the constant background was removed; the isointensity contours are plotted with the 50% contour bolded. Using another embodiment of FIG. 4, a second specimen was examined. The second specimen was also mercerized cotton and was 130μ in diameter (Coats and Clark #50) similarly treated with benzoporphyrin derivative monoacid (BPDMA), a drug used for photodynamic therapy of tumors. The chicken breast was partially immersed in phosphate buffered saline and sealed with Dow Handiwrap plastic film. Here, the plot is raw data (relative intensity vs. depth (z) and cross scan (x). These strong clear signals are possible when a marker dye is used to enhance the signal of small tumors, and requires minimal signal processing to be useful to the surgeon. When the native fluorescence of tumorous tissue is observed, more complex processing is generally necessary.

In FIG. 4C, the "depth" dimension lies along the optical axis of the apparatus (the vertical axis). The horizontal "cross" dimension was perpendicular to the thread. The functional difference in these two axes is that the depth and transverse resolutions differ: the depth resolution is ≈76μ, and the transverse (cross) resolution is ≈25μ.

Although not of direct clinical interest, additional minor signal analysis will improve the measurement even further. The contours are lengthened in the depth direction. Depth resolution was approximately 50μ larger than the radial resolution, and, thus, we expect the 50% contour depth to be about approximately 100μ greater than the contour width. The actual measured difference was about 125μ. Also, because the thread is not much larger than the depth resolution, at the center of the thread, the observed probe-volume is filled with fluorescing target; whereas, at the edge of the thread, it is under filled. In these circumstances a simple deconvolution algorithm is expected to recover the cylindrical shape.

To minimize the amount of laser illumination at 633 nm which is scattered from the elements of the system 10" into the detection photomultiplier, the preferred embodiment 10" of FIG. 4A, may position the thin reflective field stop aperture carrier tilted at an angle, for example two degrees, so that illumination not passed is not reflected into the collection optical path; further, the inner diameter of the optical head assembly package may be threaded and painted with an absorbing diffuse paint so that light scattered to the walls is optimally absorbed or blocked. A spatial filter may also be inserted in the collection path between the beam splitter 100 and the optical filter assembly 915 so that reflection from the connector at the end of the illumination coupler 32 is blocked but return fluorescence is passed.

As will be understood in part from the foregoing description and in part form the detailed discussion below, the volume microprobe of this invention enables one to detect or monitor a broad range of physiological effects or states. By way of example, the probe may be directed with depth discrimination optics to monitor skin or organ grafts. Conditions such as how well the graft is being vascularized may be readily detected, as will be the optical signatures of necrosis or of rapidly proliferating tissue (repair). Blood perfusion, hence vascularization can be measured spectrally, as can be various hemoglobins, and these measurements are resolved in depth.

Measuring the depletion of drugs used in photodynamic cancer therapy during a treatment is a particularly important application. One of the current drawbacks of photodynamic therapy techniques is that there is no reliable way to quantify the dose actually delivered to a tumor. Photodynamic therapy drugs are chemicals which, when flooded with light of the appropriate wavelength (usually red or near IR) are photoactivated and become toxic. They also collect somewhat preferentially in rapidly proliferating tissue. To date, all chemicals of this type are porphyrin derivatives related to the chemicals that cause porphyria and sun-sensitivity all fluoresce readily. FIG. 4C shows the detection of one such drug, Benzoporphyrin derivative monoacid, showing a highly selective spatial detection, when illuminated with the device of FIG. 4A.

Another application is to determine the depth and viability of burned tissue. The hardest decision for a trauma specialist to make in the treatment of burns is where and whether to debride burned tissue. If an area is likely to recover, scarring, recovery time, and infection risk will be lower if it is left alone. The best criterion for assessing such health is the depth to reasonably healthy vasculature. This may be determined by looking at native optical signatures, or preferably by looking at a marker drug through the eschar, etc. Indocyanine green is a fluorescent dye which has been used for this purpose; it is generally recognized as safe and is used as an indicator of cardiac sufficiency. When injected intravenously, it is rapidly distributed throughout the body and does not leak from healthy blood vessels. Thus by determining its depth under a burn, one could determine the depth of healthy blood vessels. Green and his collaborators at Massachusetts General Hospital have patented a technique for observing its fluorescence under excitation by first a red and then a UV probe. The UV-excited fluorescence is scattered more than the red-excited fluorescence, so a differential measurement is an indicator of bum depth. However, with the present invention, a direct and more accurate measurement is achieved by setting volume elements at different depths and observing the optical response to precisely localize the region of intact vasculature.

Figure 5:
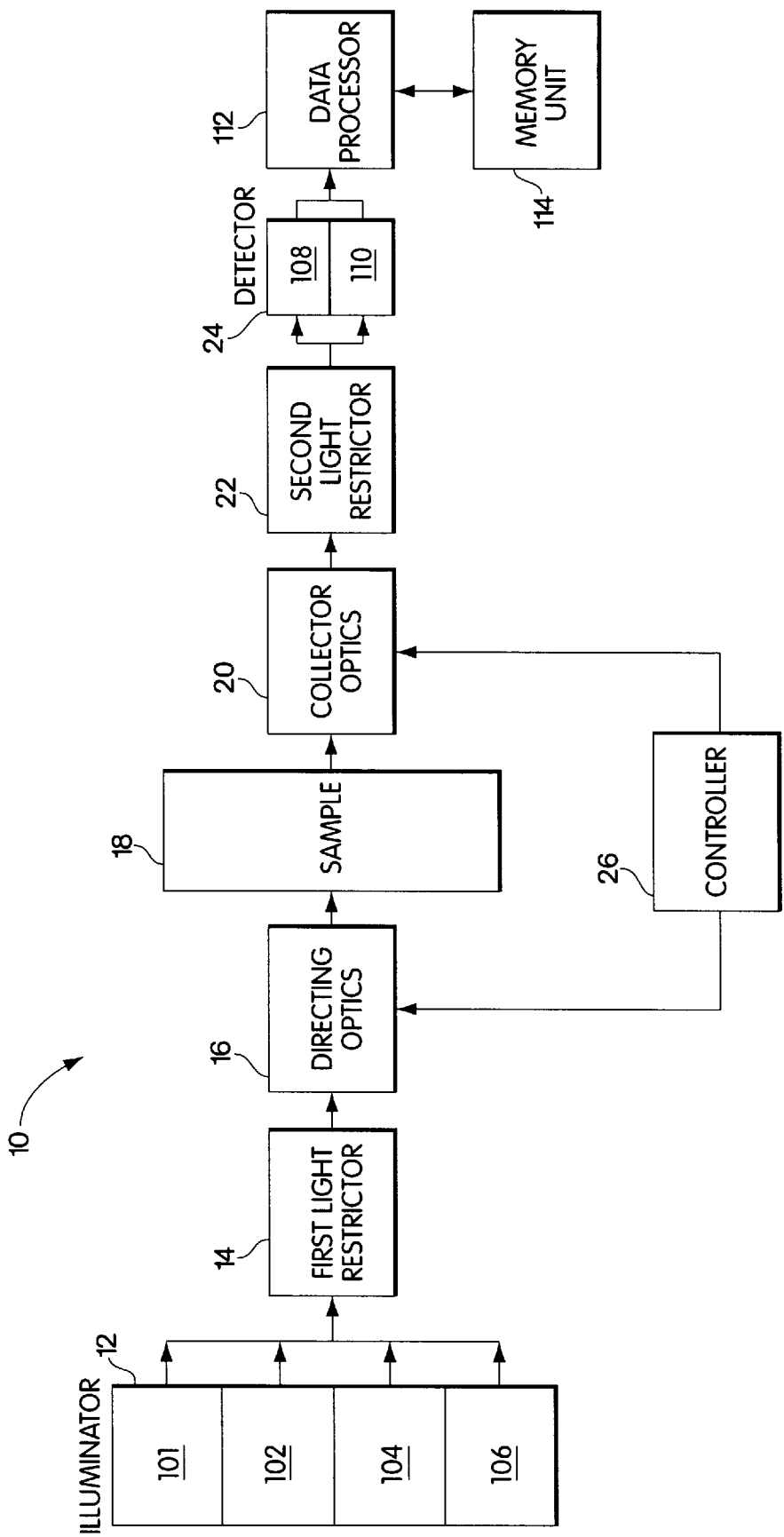
FIG. 5 shows a schematic representation of a multi-wavelength embodiment of a volume probing system according to the invention.

While the invention has been described in very broad terms of illuminating and detecting light from selected volume elements in a sample where the volume elements are defined in part by a relatively large aperture source, the invention is understood to include instruments and methods employing any known type of illumination, and indeed because of its enhanced signal levels, their sharp spatial z-axis discrimination (namely along the axis of illumination), and their correspondence in size or even shape to tissue layers or biological features of interest, applicants expect that the use of the invention will reveal significant spectral response information to be available with instruments of the present invention even using some illumination sources which have previously yielded no useful analytic information of this type. Furthermore, the invention contemplates use of a full range of detectors for receiving the collected spectral information to detect not just amplitude or power, but entire spectra or sets of spectral features. By way of example, FIG. 5 describes a non imaging volume microprobe in which an illuminator 12 contains a plurality of light sources, specifically, a nitrogen laser 101 emitting light at 337 nm, a white light source 102, a laser diode 104, and a light emitting diode 106. FIG. 5 further illustrates a detector 24 having a scanning monochromator 108 and a spectrograph 110. Illuminator 12 provides multiple different light sources for probing a volume element, and detector 24 provides multiple devices for detecting and/or plotting characteristics of the electromagnetic radiation emanating from the selected volume element. In general, illuminator 12 may generate electromagnetic radiation having wavelengths ranging from below the ultraviolet to far-infrared wavelengths, while the detector 24 and its associated data processing unit 112 may detect discrete or continuous spectral information and may further include signal conditioning elements for filtering, integrating, time-shifting and differentiating, as well as for further processing the collected response signal. In particular, data processor 112 also include means to carry on analysis on a set of training specimens, for example to carry out multivariate statistical analysis, so as to derive a correlation transform matrix, and means for applying the transform matrix correlating responses from a specimen outside the training set to a number of pathological states that could be present in said specimen outside said training set.

In operation, light emitting diode 106 of this system generates a red sensing or targeting light that provides a visual aid for identifying the general area within sample 18 that is illuminated by the light emitted from system 10 and may be used as a targeting or steering beam of radiation for generating steering signals to redirect the direction in which system 10 is pointing, and thus to define or stabilize the area in which the selected volume element being examined is positioned. Suitable beam steering arrangements which operate, for example, with galvanometer-controlled steering mirrors to aim an image or feature, and controlling one or more steering mirrors in response to displacement are known in the art. White light source 102 produces a broad band signal, while the nitrogen laser 101 and the laser diode 104 each generate electromagnetic radiation having particular wave lengths. For example, nitrogen laser 101 can generate ultraviolet light with a wave length of 337 nanometers and laser diode 104 can generate a beam of light having a wave length of 780 nanometers, while white light source 102 can produce a beam of light containing a plurality of wavelengths and useful for eliciting optical responses including absorption and reflection responses in a broad band of the electromagnetic spectrum.

Nitrogen laser 101 can be used to excite the material within the volume element 46, and cause it to fluoresce. Amplitudes and wavelengths of fluorescence that emanates from the targeted volume element will bear important diagnostic or analytic information characteristic of the volume element, and the collection system together with the data analysis system can use the fluorescence response to provide diagnostic information on the volume element. White light source 102 and laser diode 104 can also be used to generate beams of radiation which interact selectively with the volume element 46 so that its response to the radiation can be collected and diagnostic information derived from such responses. Such responses can include scattering, absorption and reflection characteristics. In some embodiments of this invention, when using a non imaging volume microprobe such as described in FIG. 2 in conjunction with a plurality of light sources and detectors as described in FIG. 5 the angular spatial distribution relative to the illuminating beam of the response of the targeted volume element can be used for analytic purposes as well. Such an application would involve, for instance, the continuous monitoring of the growth process of bacteria in fluid or gelled growth media, or the monitoring of complex fermentation processes.

The detector portion 24 of the instrument of FIG. 5 includes a scanning monochromator 108 and a spectrograph 110 for analyzing radiation response emanating from the targeted volume element 46. Detector 24 analyses the radiation coming from sample 18 by first passing the radiation through spectrograph 110 or monochromator 108. Spectrograph 110 disperses the collected radiation beam into a spectrum for further analysis, and monochromator 108 isolates particular regions of the spectrum from the collected dispersed beam of radiation to determine their intensity or other properties. Once spectrograph 110 or monochromator 108 have isolated the particular wavelengths or spectral region of interest, this further analysis can take place. In particular, the detector 24 system can determine the particular wavelengths of light contained in the collected radiation, and the characteristics of the detected wavelengths. Characteristics of interest at particular wavelengths include: the intensity of the radiation at the wavelength; the polarization direction, if any, at the wavelength; and the phase shift at the wavelength. Other characteristic of interest in the collected radiation includes its fluorescence life time, when the line being observed is fluorescent, and wavelength shifts of the emission peaks at the wavelengths of interest.

For control, storing and analysis of the detector data, FIG. 5 also illustrates a data processor 112 coupled with detector 24, and a memory unit 114 coupled with data processor 112. Data processor 112 can be, for example, a general purpose programmable computer, and the memory unit 114 can be an electronic storage device such as a digital memory chip, a floppy or hard disc, a magnetic tape, or a read/write compact disc. Data processor 112 can also contain a read only memory on which resides a library of correlation transforms vectors or matrices, the former used in conjunction with automated diagnostic of single pathologies and the latter in the automated diagnosis of a plurality of pathologies. It may further contain a set of computer instructions, modules and subroutines for tagging a set of samples, adding data fields provided by keyboard input and deriving one or more correlation transforms which are then stored, possibly updated or modified, and maintained in a library, as is described further below.

In general, the invention is intended to operate at least partially to record and generally also compile and analyze the responses it collects. In some low cost embodiments of the instant invention, only diagnostic prediction of pathologies is provided, namely, the system is equipped with a library of correlation transform vectors or matrices for specific diagnostics functions, and the system only registers the signals $I_{ij}$ and calculates functions $F(I_{ij})$ required to provide a diagnostic score $C_j$, for a volume element j, as is further described below.

In broad terms, the output from detector 24 is fed to the data processor 112, which can process the output from detector 24 or can store the data in memory unit 114 for processing at a later time. Data processor 112 can also compare a first data set obtained from detector 24 with a second data set obtained from memory unit 114. For example, data processor 112 can calculate correlations between a first data set representative of the material being probed and a second data set in memory unit 114. In accordance with a preferred embodiment of this aspect of the invention, the second data set may amount to a library of optical response data or most preferably includes a mathematical model abstracted from such a library, as described below in the section entitled, "Methodology and Operation of the Non Imaging Volume Microprobe."

Memory unit 114 can be used to store a large body of data about particular materials. For example, memory unit 114 can store data concerning the characteristics of light which has interacted with a particular type of biological tissue, or memory unit 114 can store data concerning the characteristics of light emitted by particular types of biological tissues in response to excitation by each of a set of wavelengths of light, or can store such spectra indexed by tissue depth, or other complex multidimensional spectral data derived from a prior set of observations.

Memory unit 114 can further store information associating particular characteristics of light obtained from a biological tissue sample with a particular diagnosis. For example, the ratio of light reflected at one wavelength to light reflected at a second reference wavelength can be associated with a cancerous tissue growth as in certain known observations, or may be associated with a clinically relevant condition such as a thickening of one layer of tissue, a precancerous metabolic change, or a malignancy, based on correlation with the spectral library and previous clinical characterizations. Thus, correlation with annotated or stored digitized spectra may provide a diagnostic judgment, even without the identification of any specific individual spectral features, such as peaks or absorbance bands, that have been required for diagnosis in the past.

Methodology and Operation of the Non Imaging Volume Microprobe

In the prior art, spectral and chemical analysis of complex and heterogeneous matrices was hindered by the inability to limit the response obtained from such matrices to regions with a high degree of homogeneity. A large group of microprobes were developed to handle this problem, and indeed, there exist electron microscopes and ion microprobes and various other devices capable of providing analytic information, both morphological and to some extent chemical (mostly elemental) on a point by point basis, or even through sections (such as with the ion microprobe) of specimens. Unfortunately these methods all require the placement of the sample in vacuum and the eventual destruction of the specimen, and furthermore these methods are not conducive to the analysis of organic materials. In vivo microprobe analysis of biological tissue poses requirements that are somewhat different than those of classical microprobes. Particularly, it is not necessary to have a resolution greater the typical dimensions of differentiated tissues, but it is desirable to have analytic tools that can be operated by personnel without specific training in the analytic arts, such as physicians, process control personnel and other professionals. With the invention of the non imaging volume microprobe as set forth in the present application, such microprobing of biological tissues in vivo, and other specimens in their natural environment is achieved. There are numerous approaches by which the response data from such a non imaging volume microprobe is useful, and without limiting the scope of the instant invention, we describe herein some of these methods.

In one embodiment of the instant invention, responses from a volume element, which represent or at least contain specific signatures of the interaction of the material within the volume element with the impinging radiation, are presented in terms of received light intensities for a set of various discrete wavelengths, or wavelength bins or as a spectrum of the response. A researcher trained in the specific analytic art can then use these spectra to recognize or deduce important information about the volume element from his knowledge of the impinging radiation and the modes of interaction of that radiation with his target material. A variety of analytic tools such as software programs designed to conduct spectral peak fitting, or spectral deconvolution can be directly applied to further increase the researcher's basic understanding of the underlying interactions and provide the researcher information on the chemical, morphological and physiological nature of the target volume element. This in accordance with basic principles known in the art, with the change, in accordance with the present invention, that the data provided to the researcher are directly taken by the instrument and derived from a well defined volume element, rejecting interferences and response weakening of the relevant spectrum from light originating outside the target volume element. Thus background noise no longer drowns out the signal of interest and hinder the researcher's ability to differentiate specific features within a largely heterogeneous sample. Because of this ability to obtain a clean spectrum from a heterogeneous sample, the non imaging volume microprobe of the instant invention can apply its collected volume response data as input to a relatively simple numerical analysis module of conventional type to carry out classical absorption spectroscopic analysis, scattering analysis, fluorescence analysis, Raman scattering and other parametric or characterizing analysis without the complications that occur when applied to less well-defined or to buried signals.

In another embodiment of the instant invention, directed to users that do not possess the technical skills to derive meaningful conclusions from raw responses observed, the system is equipped with a library of correlation transforms dedicated to the users special diagnostic or analytic needs, so the system is essentially pre-calibrated for specific analytic tasks. The method of calibrating the non imaging volume microprobe is further detailed herein.

For simplicity of the following description, we will assume that the goal of the method is to calibrate a non imaging volume microprobe for the diagnosis of the presence or lack of a certain condition in particular tissues that are accessible to optical visualization, either on the external skin, or in the cervix, or in other cavities accessible via endoscope or laparoscope, such as the various segments of the gastrointestinal tract (starting from the mouth, through the esophagus and the stomach, and, by rectal examination, the colon), or various organs in the peritoneal cavities that are accessible via exploratory laparoscopy. In may of these situations, a physician who is not a trained spectroscopist, presently must view the suspected tissues, and when discoloration or other morphological abnormalities are present, must excise samples from such areas and send them to a pathology laboratory for microscopic examination to determine the presence or lack of cancer pathology, as well as the stage of possible cancer. The present invention provides, during the visual examination, a non-invasive optically derived diagnostic scoring to determine the nature of the suspected pathology of the suspicious target tissue, so that immediate action can be taken, if necessary, and in any case avoiding unnecessary excision of tissue for biopsies. Moreover, when calibrated as described below, the non imaging volume microprobe of the instant invention provides automated diagnosis of such viewed tissues by a physician, without the need for a pathologist to examine such tissues under the microscope.

In order to calibrate the non imaging volume microprobe for a specific pathology, we first select a training set of specimens for the specific pathology. The term "training set" is used herein to denote a group of tissue specimens on which very exacting determination of the state of each specimen has been previously conducted in a pathology laboratory. Furthermore, prior to excision for such biopsies, each specimen in the training set preferably has been subjected, in vivo, to illumination and detection with the non imaging volume microprobe of the instant invention to provide a stored spectral response record. For the purpose of this description, let us assume that the target volume elements of this training set (those tissues that are later subjected to a pathology laboratory determination of their pathological state) are investigated with the volume microprobe of FIG. 5. They are illuminated with both a laser UV source (101) and a broad band white light source (102). Let the intensities of the responses to the UV and white light excitations of the targeted volume element within the specimen j be denoted $J_{uj}$ and $I_{ij}$ respectively, where u and i are central wavelengths within spectral bands of the spectral responses to the UV and to the white light excitations respectively. For example, the $J_{uj}$ may be fluorescence and the $I_{ij}$ may be backscatter responses, respectively. These data are stored in memory unit 114 for future analysis. The training set are excised after recording the responses obtained with the non imaging volume microprobe and pathological determination of the state of each specimen are recorded in the form of scores $C_j$, where j is the identity of the specimen and $C_j$ is a number selected according to the specimen state on a monotonic scoring scale, for example a single-axis scale of zero to ten, where zero denotes normal tissue and ten corresponds to a characterization as a fully entrenched and deep cancerous tissue change. This training set is used to calibrate non imaging volume microprobes for future determinations of the presence or lack of each of the tissue pathologies represented in the set, so it is important that great care be taken in arriving at an objective determination of the pathological state of the training set. Preferably, the same samples are examined microscopically by a number of independent pathologists in a blind experiment, and only such specimens for which there is a valid threshold of agreement between the various pathologists are included in the training set.

Once the scores $C_j$ of the specimens in the training set have been carefully determined, the values of $I_{ij}$ and $J_{uj}$ previously stored in memory unit 114, are used to set up a set of j correlation equations:

$$\Sigma a_i F(I_{ij}) + \Sigma b_u F(J_{uj}) = C_j \tag{1}$$

The band widths around the wavelengths i and u of the collected narrow band responses to white light and UV light respectively, may generally be set between 5 and 50 nm, depending on the spectral resolution achievable or desirable in the system's detection monochromator 108 or spectrograph 110.

The selection of the functions F depends to some extent on the nature of responses received. When collecting almost featureless spectral responses (namely a spectral response which is relatively smooth and changes slowly with the wavelength), then one may select the response intensities, or normalized intensities, namely, $F(I_{ij})=I_{ij}$ or $F(I_{ij})=I_{ij}/K$, respectively, where K is either the maximum response in the received spectrum or K the response at a predetermined wavelength (which, for example, in biological tissues, may be a response associated with the presence of water, or of hemoglobin). When the expected spectrum contains a number of sharper features, one may set $F(I_{ij})=(dI_{ij}/d\lambda)I_{ij}$, where $\lambda$ is the wave length.

The data processor 112 next performs a regression analysis to minimize the number of wavelengths i and u used to obtain a valid correlation and to solve the set of minimized equations (1) for the correlation constants. This regression analysis is carried out using the j equations obtained experimentally, using in essence the correlation constant as unknowns, for which a solution having the best correlation is sought. The minimization is carried out to extract a minimum number of wavelengths whose responses $I_{ij}$ and $J_{uj}$ provide satisfactory correlation with the phenomenon being measured. It should be appreciated that during the calibration process, a greater amount of data is collected than absolutely necessary, and much of these data are interrelated. In mathematical terms, the minimal set may be a basis of responses for this tissue. Once a minimal set of responses has been determined, this allows the taking of a minimal set of responses during subsequent actual diagnostic use of the non imaging volume microprobe (e.g., responses at a minimal number of narrow wavelength bands), and thus accelerates the procedure.

The methods used for obtaining the minimal set of wavelengths and the associated correlation coefficients $a_j$, and $b_u$ are well known in the prior art and include multivariant linear regression analysis and univariant linear regression analysis. Other statistical tools such as neural networks analysis are also available and can also be applied to this task. These statistical tools have been reduced to simple software programs such as those sold or available, for instance, under the name STATISTICA by Statsoft, Inc. or PREDICT by Neural Ware, Inc.

In general, we denoted by the values $I_{ij}$ and $J_{uj}$, the responses of the volume element to white light and UV excitation respectively. Other responses might be used to characterize the volume element 46; more generally, we denote all responses which are responses from volume elements that correlates with certain pathologies $R_{ij}$. We find that it is sometimes advantageous to include as part of the responses $R_{ij}$, i.e., to include as a data field in the memory record representing $R_{ij}$, other information about a volume element which was not determined with the help of the non imaging volume microprobe but still contributes to improvement in the correlation between the observed responses and the pathologies diagnosed. Such information might include general medical record information, such as classification of the subject in which the volume element resides, including, but not limited to features like sex, age, race, and weight. Such information, when its inclusion in the regression improves the confidence level of the regression, can be included as additional "artificial" responses $R_{ij}$. The index i therefore represents the type of response obtained whether it is obtained with the non imaging microprobe (one or more types of responses as well as the spectral band from which the response is registered) or by other means such as extrinsic patient, population or source data.

The set of equations (1) from which the correlation coefficients are derived can thus be simplified to be:

$$\Sigma a_i F(R_{ij}) = C_j \quad (2)$$

For notational simplicity we call the ordered values $\{a_j\}$ the correlation vector (a) for the pathology C, and the ordered responses $R_{ij}$ the responses vector $(R_j)$ for volume element j in the training set. The functional responses vector $(F(R_j))$ is similarly defined as the ordered functions of the responses elements in the responses vectors $(R_j)$. Similarly, the ordered scores $C_j$, can be termed the pathology score vector (C) for said training set. The process of calibrating the non imaging volume microprobe for a given pathology C, consists therefore of compiling the all the response vectors $(R_j)$ and their corresponding pathology score vector (C) and from these data, after generating the functional response vector $(F(R_j))$, determining a minimal correlation vector (a) which is the calibration vector of the non imaging volume microprobe. These mathematical constructs are then stored in memory, together with basic software for applying them to a new response.

Clinical operation of the probe proceeds as follows. When a calibrated instrument is now used to determine the extent of a given pathology C in a volume element outside the training set, (where this new volume element is denoted k) the responses vector $(R_k)$ is registered by the instrument on the volume element k, and to the extent that some of the responses $R_{ik}$ are artificial responses (e.g., extrinsic data from medical records, such as sex or race), these are entered into the data processing unit 112, and the score for the pathology C for volume element k, $C_k$, is predicted by obtaining the product of the correlation vector (a) with the functional responses vector $(F(R_j))$, namely: $C_k=\Sigma a_i F(R_{ik})$. Thus the use of the calibrated non imaging volume microprobe on a volume element k whose pathological state $C_k$ is unknown, allows for the immediate and automatic testing and diagnosis of the pathology C in the volume element k by application of the stored mathematical operator to the observed Response vector.

It should be appreciated by persons trained in the art that the non imaging volume microprobe of the instant invention can be calibrated to diagnose a plurality of different pathologies $P_m$, where each m denotes a specific pathology. When used in this fashion, the task of calibrating the instrument for this plurality of pathologies consists as before of taking a training set of j responses $R_{ij}$ and scores $P_{mj}$, where i denotes the bandwidth of the response or the type of artificial response, j the volume element or the specimen in the training set, and $P_{mj}$ the score for pathology m on specimen j. As before, during calibration we obtain a number of correlation vectors $(a_m)$, each for the specific pathology m. In operation of the calibrated non imaging volume microprobe, the correlation vector (a) mentioned above is now replaced with a correlation matrix $\{a\}$ whose elements are $a_{im}$, the functional responses vector $(F(R_k))$ for an uncharacterized specimen, k, is replaced with the matrix $\{F(R_k)\}$ whose element are $F(R_{imk})$, and the diagnostic results are given as a vector $(P)_k$ whose elements are $P_{mk}$ obtained by the product of the correlation matrix $\{a\}$ with the functional responses matrix $\{F(R_k)\}$. Thus, once a set of diagnostic conditions of interest has been identified and a suitable training set of responses processed to generate these matrices, the diagnostic score for each condition is computed automatically for a new sample by a simple matrix operation on the volume element response.

It should also be appreciated that in the practical embodiment of this method of analysis, the correlation created will use the same responses, or at least a partially overlapping set of responses—e.g., magnitudes of detected radiation in a specific set of defined wavelength bands—for different pathologies. Thus only a vector of responses ($R_k$) (having elements $R_{ik}$) is required which includes the minimal set of responses from volume element k to obtain diagnostic scores $P_{mk}$. The matrix $\{a\}$ can also be termed the correlation transform matrix, since it transforms one set of measurable values (or observables), to another set of numbers or values, which are the desired pathology scores. This is achieved by multiplying the correlation transform matrix, $\{a\}$, with the vector, the functional responses vector, ($F(R_k)$) to obtain a transformation of the responses vector ($R_k$) to a vector of diagnostic scores $(P)_k$.

It should be further appreciated that by probing a plurality of adjacent volume elements in the optical axis direction (the z axis) one obtains the penetration depth of certain pathologies by plotting the scores $P_m(z)$ for the pathology m as function of depth z. Similarly, an artificial three dimensional image of the pathological state of an area can be obtained by repeating the procedure for a number of adjacent volume elements in the xy plane (the plane orthogonal to the optical axis of the non imaging volume microprobe), where the gray scale or the color for each volume element correlates to the diagnosed scores $P_m(x,y,z)$.

Since, as described above, the volume probe collects the response from a well localized area, this manner of plotting "pathology gradients" within a sample may elucidate the growth processes involved in diseased tissue, and is expected to elucidate complex relationships between such processes and different surrounding tissue types.

A correlation transform method such as exploited herein, for predicting diagnostic or analytic information on an unknown specimen by correlating optical responses of a training set to independent determination of diagnostic or analytic data on the training set, has been shown by Rosenthal to work well on artificially homogenized samples that are large enough to provide a set of responses possessing large signal to noise ratio. It is surprising that the expanded, but similar method of the instant invention yields good correlation on very minuscule volume elements in vivo. In classical spectroscopy, for instance as described by Alfano, spectra or optical responses of diseased tissues are compared to similar spectra or responses of healthy tissues to attempt a diagnostic reading on the target tissue. This method generally is not sensitive and robust enough for in vivo clinical application because of the large variations encountered between subjects and the nature of the tissue examined. When using the above described correlation transform method, we purposefully avoid using comparison of spectral responses in a target tissue to the responses of any existing (healthy or pathological) tissue. Since no one specific tissue can represent all the variations encountered between subjects, subject to subject variations cause spectral distortions that invariably weaken the ability of the prior art to obtain robust diagnostic determination of pathologies. Furthermore, by our inclusion of non optical responses together with the optical responses as part of the correlation transform algorithm, we in essence build a completely artificial model (based on the training set) of the pathology, which by itself is never reproduced in any one subject or tissue. This novel approach coupled with the spatial filtering of the optical responses to a small volume element, are believed to account for the success of the invention in predicting diagnostic states of tissues in vivo.

It will be understood that the enhanced information content of the detected optical responses may be observed by other processing regimens known to be useful for analysing data sets. Thus, for example, rather than the particular correlation regimen described above for deriving transforms T to evaluate particular pathologies, the instrument may apply transforms derived by any of the processes of peak matching, spectral deconvolution, spectral ratio matching, self normalization, Fourier transform analysis, discriminant analysis, linear univariate and multivariate regression analysis, non-linear univariate and multivariate regression analysis, partial least squares regression analysis, principal component analysis, and neural network analysis. As with the above described embodiment, it may apply these processes to directly compare a sample with a stored data set, or may apply a stored transform T developed by such a derivation process.

It should be emphasized that the enhanced localized information content of the optical responses collected by the present invention may allow discernment or distinction of states which need not be so extreme as to amount, for example, to an entrenched or established disease state. Indeed, slight degrees of differentiation, transient metabolic or circulatory effects and other such conditions may all be revealed in the collected spectral data. Thus the detected condition may be one or more of the set of burn, necrosis, inflammation, tissue repair, graft healing, graft rejection, lesions, cancer, cancer precursors, benign hyperplasia, benign dysplasia, tumors, the presence and concentration of specific compounds wherein said compounds are naturally occurring agents and their metabolites, the presence and concentration of therapeutic and illicit agents and their metabolites, and other such pathologies or conditions. Furthermore, as applied to samples of non-biological material or pure chemicals, the responses may be processed to detect diverse physical or physico-chemical phenomena such as spectral redistribution, polarization shift, temporal shift, spectral shift, Zeeman splitting, Stark splitting, phase shifting, shifting of the frequency and amplitude modulation of the intensity of the emanated light with respect to the illumination.

Also, the nature of the collected light may vary depending on properties of the sample and the optics involved, to selectively detect one or more of scattered illumination, transmitted illumination, attenuated illumination, reflected illumination, Raman scattered illumination, autofluorescence stimulated by the illumination, and marker and therapeutic agent fluorescence stimulated by the illumination. The basic illumination in turn may be provided by a broad band source, a narrow band source, a substantially monochromatic source, a light emitting diode, a laser or a frequency and/or amplitude modulate intensity source.

Exemplary Instruments

Figure 6A:
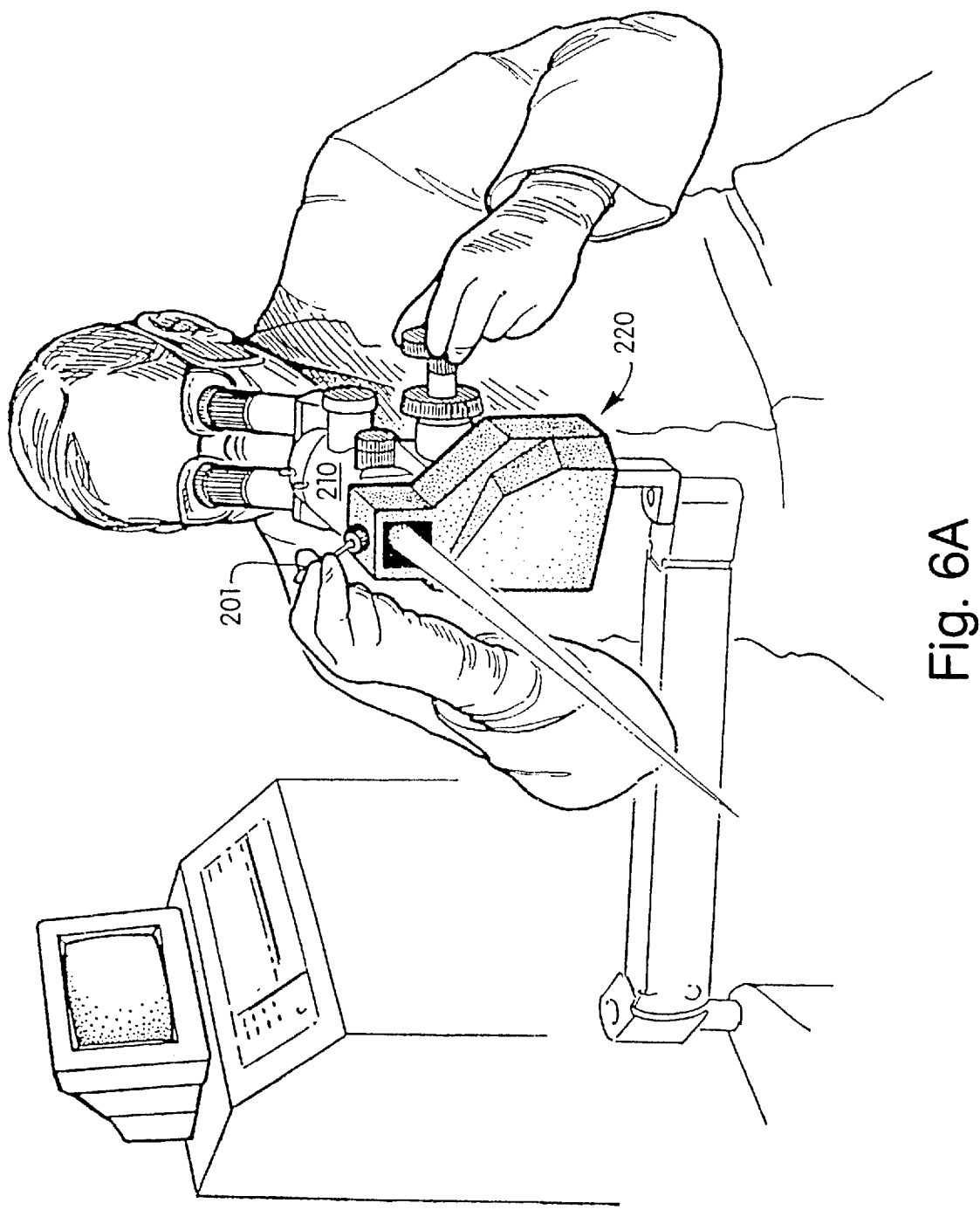
FIGS. 6A and 6B illustrate an embodiment adapted to a colposcope.
Figure 6B:
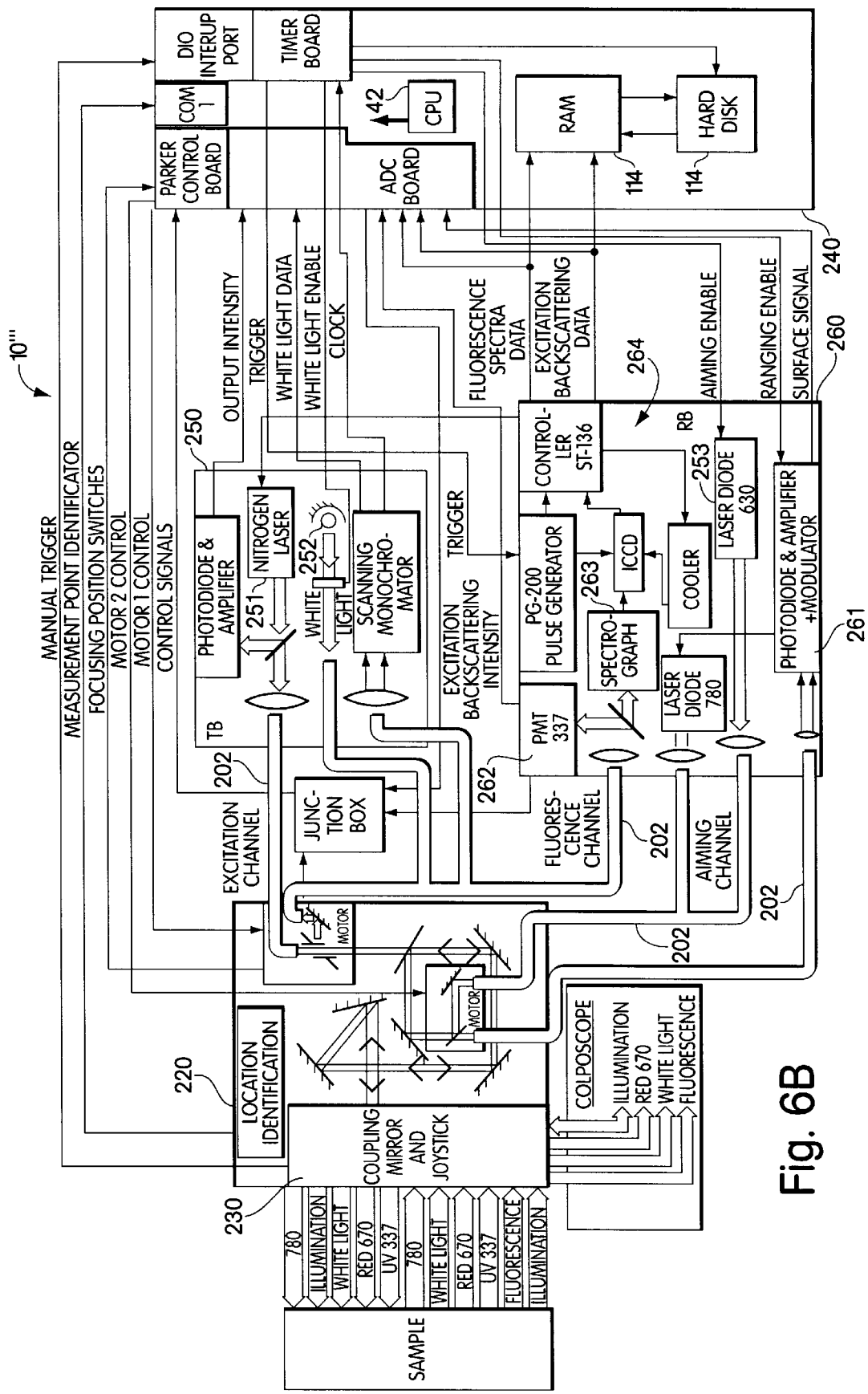

Returning now to a discussion of instrumentation of the present invention for particular applications, FIGS. 6A and 6B illustrate a colposcope embodiment of the invention.

As shown in FIG. 6A, a non imaging volume microprobe 220 of the present invention attaches to the patient-side dovetail of a conventional colposcope 210 and couples its illumination and collecting paths into the objective path of the colposcope so that the viewing gynecologist may see and identify an area where diagnostic scoring of specific tissue is desired, both at the surface observed and to some depth below the surface. In this instrument, the colposcope has an effective working distance of about 30 cm and the optical head 220 is aligned and attached to the colposcope housing to maintain stable alignment with the colposcope, while small steering mirrors inject or catch the probe beams. A joystick 201 and coupling mirror allow the optical paths of the non imaging volume microprobe to be steered within the colposcopic field of view and overlap this field of view. The head design permits mounting from either side to suit the handedness of the gynecologist, so that the ColpoProbe™ does not intrude into the space used by the gynecologist for manipulating instruments like biopsy forceps. The remainder of the instrument is connected to the optical head by a set of optical fibers approximately 5 m long This allows the bulky portion of the system to be well out of the way.

In operation, a gynecologist would use a non imaging volume microprobe that has been precalibrated, namely, it has in its memory a correlation matrix {a} as described above which correlates light responses collected from target volume elements in the cervix with any of a number of possible pathologies such as, but not limited to, inflammation, repair, high and low grade squamous intraepithelial lesions, or neoplasia. The gynecologist points the non imaging volume microprobe to the desired zone, where a pathology is suspected. The gynecologist may also enter "artificial" responses, i.e., non-optical information such as age, if postmenopausal, how long, if premenopausal, time in the menstrual cycle, or other extrinsic medical-record-type information. These artificial responses correspond to further variables which may be values on which the correlation transform operates. The gynecologist then starts the registration of the desired responses from the subject zone with the non imaging volume microprobe, including z scanning of the depth of the suspected tissue pathology. The instrument samples and holds the observed response when triggered, or it may be configured to automatically sample a plurality of responses in a local pattern. Once the non imaging volume microprobe has manually or automatically taken the requisite number of responses, the correlation transform is applied to the responses vector to transform it to a vector of scores for the pathologies for which the instrument was calibrated. This is achieved in the processor 112 by calculating the vectors of functional responses ($F(R_k)$) for each volume element, k, sampled by the probe, and multiplying it by the correlation transform matrix {a} which resides in memory 114 and was derived during the calibration of the non imaging volume microprobe.

One prototype instrument for volume-limited enhanced signal collection of tissue has been developed for better biopsy of cervical cancer and differential diagnosis of cervical abnormalities. This instrument, to be sold under the trade name ColpoProbe™ is shown schematically in FIG. 6B as instrument 10′″, and is designed for non-contacting clinical applications of spectrophotometric measurements to this diagnosis task. The ColpoProbe™ examines spectral signatures of tissue in different states of health, for example by measuring and processing autofluorescence and spectral backscatter measurements from volume elements of a size on the order of a few hundred microns on a side or bigger, interesting to the gynecologist at colposcopic working distances, typically 300 mm. The measurement mode and the data processing each figure substantially in providing clinically useful data.

FIG. 6B illustrates the module 220 in greater detail. A plurality of fibers 202 couple various source or detector elements to positions within the module, and various position switches and motorized controls move the illumination and collection fiber assemblies to maintain a desired focal distance and control their mutual overlap in the specimen so as to define a selected probe volume as shown in FIGS. 3A–3C. An assembly 221 of relay mirrors in the optical head 220 couples these elements into the optical path and maintains different sources and paths separate, allowing one or more illumination sources to be switched in, and collected light to be conducted back to the detector assembly, without interference. A curved coupling mirror acts as the common front objective assembly for the analyzer and viewing optical paths. Notably, following the basic light sources and their relay or coupling fibers, all beam-forming and beam directing elements are reflective, thus avoiding the chromatic aberrations of refractive optics. The various fibers coupling the light sources to their respective relay lenses may be of relatively large diameter, for example 100–300 $\mu$m, and serve as large aperture sources. The fiber ends may be shifted by stepper motors to laterally shift, and to advance or retract the depth of focus in the target tissue.

FIG. 6B also shows other major components of the instrument 10′″ as well as the optical head 220, spectral sources, a spectral measurement section, a control computer 240, and analysis software.

The optical coupling between the ColpoProbe™ and the colposcope is mediated by a wavelength-selective aiming mirror 230 which is controlled by a joystick 201 and does not block the field-of-view. This makes colposcope operation "transparent" to the gynecologist when the ColpoProbe™ is not actuated, i.e., the colposcope can be used as if the ColpoProbe™ were not mounted and there are no noticeable visual or mechanical effects. When actuated, the ColpoProbe™ enters either an aiming or measuring operating mode, selected by convenient push-buttons. The joystick allows the physician to select a sample point within the colposcope field-of-view by using a marker beam projected by the ColpoProbe™. In the aiming mode, the gynecologist moves the pointing beam by manipulating the joystick to select a site for examination. The physician then selects the measurement mode. After a sample point is selected, instrument pointing is held fixed and a depth scan is made from 2.5 mm above to 2.5 mm below the aiming point.

The aiming light remains on, so that, if desired, it is simple to precisely biopsy the spot selected. Also, because multiple biopsies are frequently performed, a microphone is installed in the optical head so that the physician can identify the location of each sample as it is taken.

The ColpoProbe™ employs four optical channels to interrogate the cervix. An illumination channel 231 merely passes light from the colposcope's internal illumination source to the cervix and visual data from the cervix back to the colposcope, without introducing any further effects visually noticeable to the physician. A white-light channel 232 uses a broad-band 5,300 °K light source for spectral backscatter measurements. A red, 635 nm, channel 233 is the aiming channel which provides the marker beam. This beam provides a visually discernible bright spot, which shows the aim of the instrument, and may also be used for an automated tracker control feedback loop. Finally, the 337 nm UV channel 234 is used to excite fluorescence and for backscatter measurements. FIG. 6B also shows a fifth channel at 780 nm to measure the position of the volume element whose spectral signature is being measured with respect to the cervical surface. In a preferred embodiment, this function is assumed by the red channel 233.

FIG. 6B is a schematic of the device. Because of the wide spectral range covered by the several light sources, no refracting elements are employed in the optical train; this avoids significant problems with secondary spectrum associated with refractive focusing elements. In addition, these optics permit packaging of the instrument in the space available to a usual colposcope add-on. The following description proceeds generally from left to right and top to bottom of that diagram, FIG. 6B.

Among the principal components of the optical head 220 are mirrors $M_i$ for focusing the interrogating beams on the cervix, at a distance of approximately 300 mm from the colposcope objective lenses, and for necessary beam manipulation; mirrors $M_i$ are shown schematically as oblique heavy black line segments with closely spaced short ruling behind the reflecting surface. The optical head also contains wavelength-selective beam-combiners (dichroic mirrors) shown as short oblique heavy line segments without rulings. Other elements are a depth scanning mechanism for the excitation channel and a range detector.

A transmitter block 250 contains the excitation laser 251, for example a Laser Sciences VSL-337ND-S, and the 5,300 °K white-light source 252, for example a Welsh-Alyn M24E001. Also shown are a monitor for measuring excitation output energy 261 and a scanning monochromater 262, for example a Monospec 18 Spectrograph Model 479, which analyzes backscattered white light. The excitation source in the prototype is a nitrogen laser. This may be replaced with a dye laser head, if another, or more than one, excitation wavelength is needed.

The nitrogen laser is pulsed, for example at 25 times per second; during the intervals between its 5 ns pulses, the white-light, aiming, and ranging sources are independently pulsed under computer control.

The receiver block 260 contains the aiming and position monitoring channel source 253, for example a 635 nm laser diode, the position monitoring receiver 261, a 337 nm backscatter receiver 262, and the fluorescence spectral analyzer 264, which may be, for example an Acton Spectropro 150 and a Princeton Instruments Spectral Multichannel Analyzer with an intensified CCD detector package model CCD576MGE.

The control computer 240 integrates the operation of the various sub-assemblies, for example through the use of National Instruments LabView® software. The computer controls system operation and digitizes and stores raw data for further analysis. In addition, the processor and memory of control computer 240 may also perform the functions of the processor 112 and memory 114 of FIG. 5.

Figure 7:
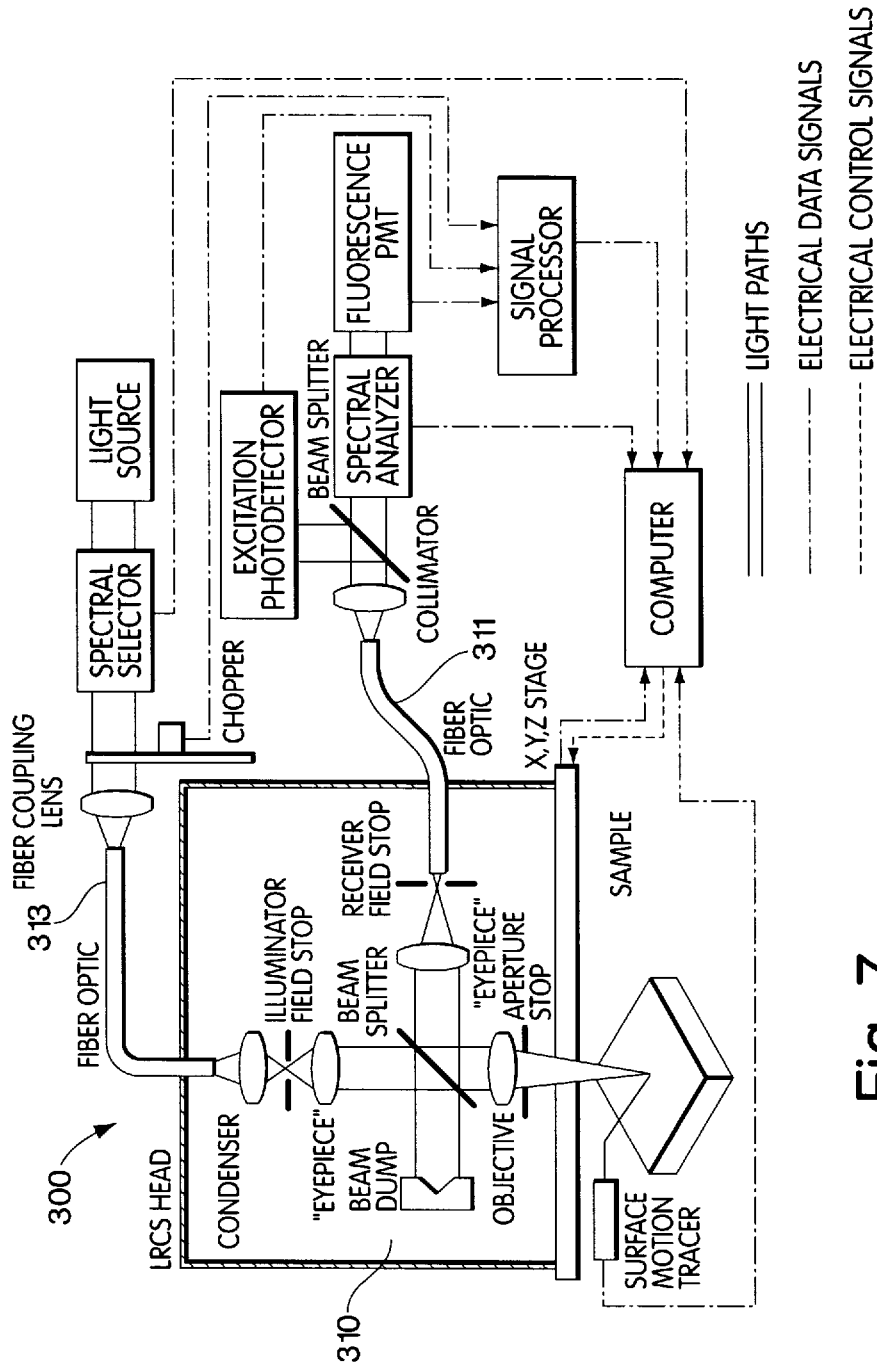
FIGS. 7 illustrates an embodiment adapted for three-axis scanning of a sample.

FIG. 7 shows another embodiment of an optical probe module 300 in accordance with the present invention. Module 300 is implemented in a single housing 310 containing the basic optical beam defining elements previously described, and coupled by input and output fiber optics 313, 311, to the illumination and detector portions of the apparatus, respectively. The unit 310 is shown as mounted on an x, y, z stage, and a computer controls the chopping of the input beam, spectral selection, stepping of the apparatus over a sample, and recording an analysis of the received illumination such that many hundreds of measurements on different probe volumes may be acquired over a short time to provide a spectral profile throughout the sample.

Figure 8:
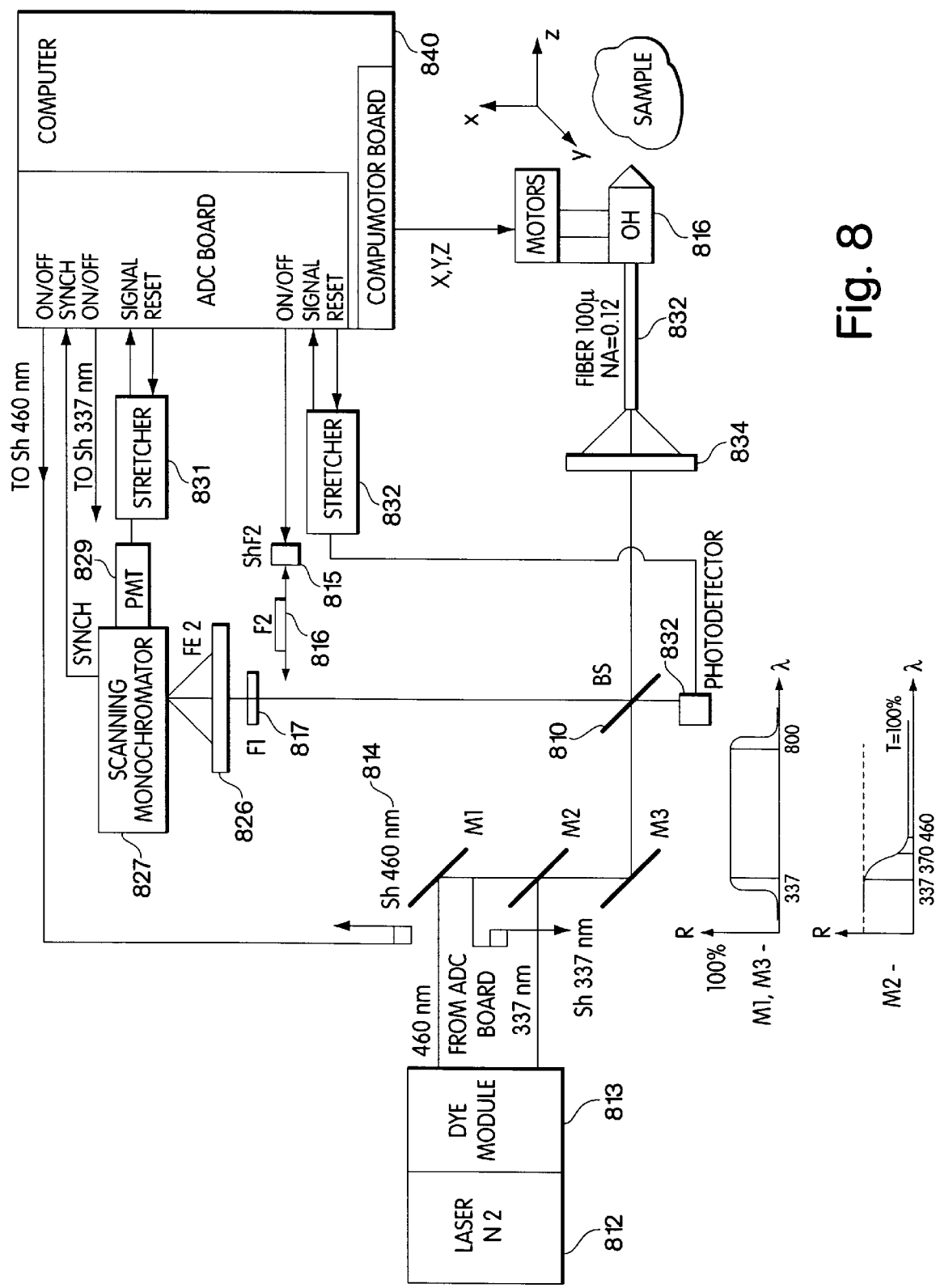
FIG. 8 shows an embodiment for probing neoplasia confined to the epithelium of muscosal tissue.

FIG. 8 is another embodiment of a prototype non imaging volume probe built by the applicants for probing early cancers, which in this case are cancers originating in mucosal tissues, and specifically for detecting autofluorescence signals from neoplasia confined to the epithelium of the mucosal lining of body cavities, while specifically rejecting interfering signals from collagen in underlying stromal tissue. The embodiment of FIG. 8 is intended to probe autofluorescence excited by two wavelengths; 337 nm and 460 nm. The illuminator 812 is a pulsed nitrogen laser at 337 nm with an attached dye laser module 813 for generation of 460 nm excitation. A shutter mechanism 814 is controlled by a computer 840 to switch between the two excitation wavelengths, and a shutter mechanism 815 switches a long wavelength optical cut off filter 826 into the collector optical path when the 460 nm excitation is employed. Optical filter 826 passes collected fluorescence longer than the 460 nm excitation light but blocks scattered excitation from entering the collection spectral discriminator 827 and detector 828. Optical filter 817 blocks excitation radiation at 337 nm, but passes longer wavelength fluorescence. Photodetector 832 monitors the output of the excitation laser to permit pulse by pulse comparison of the collected signal by providing a correction signal indicative of the changes in the laser illuminator output. Fluorescence intensity follows the illumination pulse intensity, which pulse has duration of approximately 5 nanoseconds; and electrical pulse stretchers 831 and 832 lengthen the output electrical signals which are generated by these short pulses of fluorescence so that the signal processor may accurately determine the energy carried in each pulse. The wide spectral bandwidth of this implementation requires that chromatic aberrations be closely controlled, and this is accomplished by use of all-reflective optical elements; mirrors 826 and 834 are off-axis parabolic elements used to couple light efficiently into the scanning monochromator and into the optical fiber 832, respectively. The optical head 816 is an all reflective microscope objective selected for its long working distance and high numerical aperture. The optical fiber 832 couples excitation illumination into the head and fluorescence from the head into the detector optical path. Separation of the illumination and collection optical paths is accomplished by a beam splitter 810.

In addition, this apparatus incorporates a preferred implementation of the field stop in which the end of the multimode fiber 832 closest to the objective 816 is the first, as well as the second field stop. This arrangement contrasts to that of the embodiment of FIG. 6B, wherein separate multimode fibers are employed as the first and the second field stops for the ColpoProbe™ implementation.

Figure 9A:
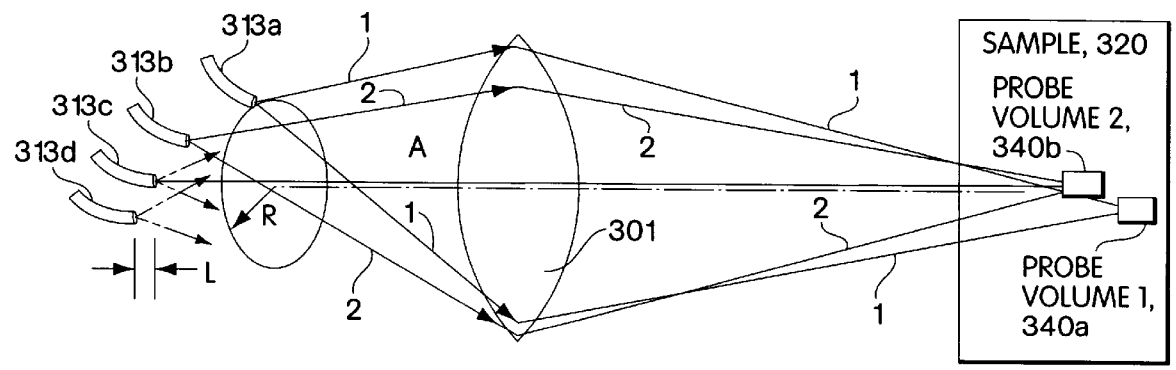
FIGS. 9A–9B illustrate an embodiment in which stationary illumination optics provide z-axis probe scanning.
Figure 9B:
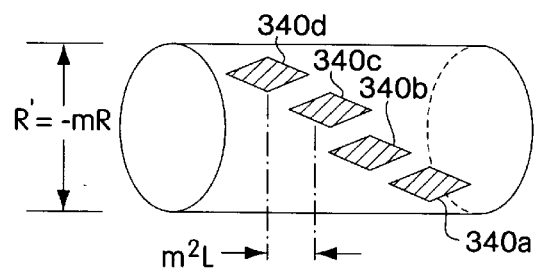

FIGS. 9A and 9B illustrate a further variation of this illumination assembly. In this embodiment, a plurality of input transmission fibers 313a, 313b . . . are disposed in a helix around a cylindrical contour of radius R with the face of each fiber offset from the preceding one by a short distance L and directing its output in the axial direction A. The cylinder of radius R may for example be a large aperture collection fiber, or may be a mechanical element such as a tube or ring. Other combinations will be evident to one skilled in the art. The output beam from each of the many fibers 313 may be focused by the single objective lens 301 into a different probe volume region in the sample 320. FIG. 9A illustrates the output beams from two fiber ends 313a, 313b with their outside edge rays denoted by 1, 2, respectively, focused into two different probe volumes in the sample. FIG. 9B shows a detail of the sample in the region of the corresponding probe volumes. Each of the corresponding probe volumes 340a, 340b . . . lie within a small cylindrical plug of radius R'=|m|R, where |m| is the magnitude of the magnification of the objective system. Furthermore each probe volume is offset along the z axis and slightly displaced to the side in a helical fashion around the plug-like probe volume by a z-axis offset of $m^2L$ where L is the original transmission fiber axial step spacing. Thus, the fixed array of fibers serve to define a sampling plug at a plurality at different depths within the sample 320. This geometry is absolutely fixed, being determined by the fixed spacing of the fiber ends and the power of the objective 301, so the sampling within the different layers of tissue is accurate and substantially independent of the stability of the instrument 301. This feature is expected to greatly enhance reproducibility of depth resolved tissue spectroscopy. In an endoscopic embodiment, the illumination and collection assemblies are necessarily defined in a much closer-focal configuration, and the probe tip itself may define the subject spacing or form part of the optics, or both.

Figure 10A:
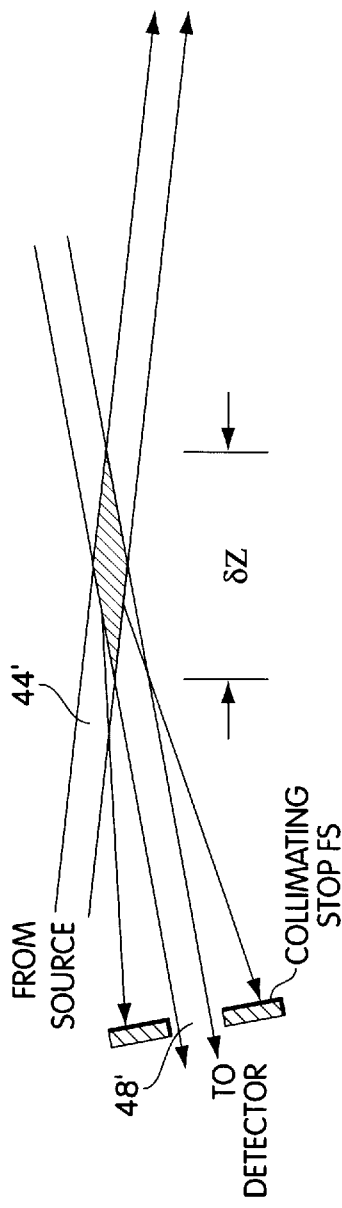
FIGS. 10A–10E illustrate alternative implementations of illumination and collection elements.

Various optical configurations may be employed to achieve non-imaging volume probe configurations with effective rejection of unwanted signals. FIG. 10A shows one such embodiment, wherein the illumination and collection beams 44', 48' are each essentially collimated. In this case, a collimating field stop FS essentially defines the width of the collection window, while the crossing angle affects the dimensions and aspect ratio of the volume element.

Figure 10B:
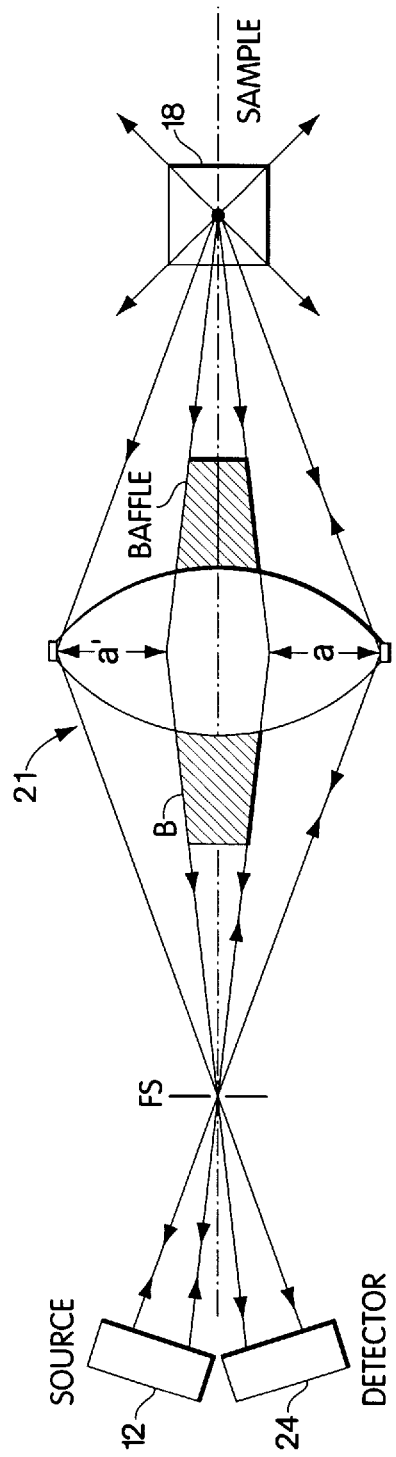

In another embodiment of the non-imaging volume microprobe configuration, the illumination and collection beams may cross, and may employ a common field stop FS, but still utilize a common objective lens assembly. This is achieved as shown in FIG. 10B. Here, source 12 and detector 24 are each obliquely directed to cross at the stop FS, while an objective assembly 21 is placed so that different portions a, a' of its clear aperture are used for illumination and collection. A baffle B assures clean separation of the two sub-regions of the shared objective aperture. At the image of field stop FS in the sample 18, the two beams cross defining a stably-aligned sheared-conjugation volume element. Other more conventional approaches to sharing of the aperture of an objective assembly may also be used, for example by using small mirrors to fold-in separate optical paths, passing through two separate field stops, into different locations on the objective lens.

Figure 10C:
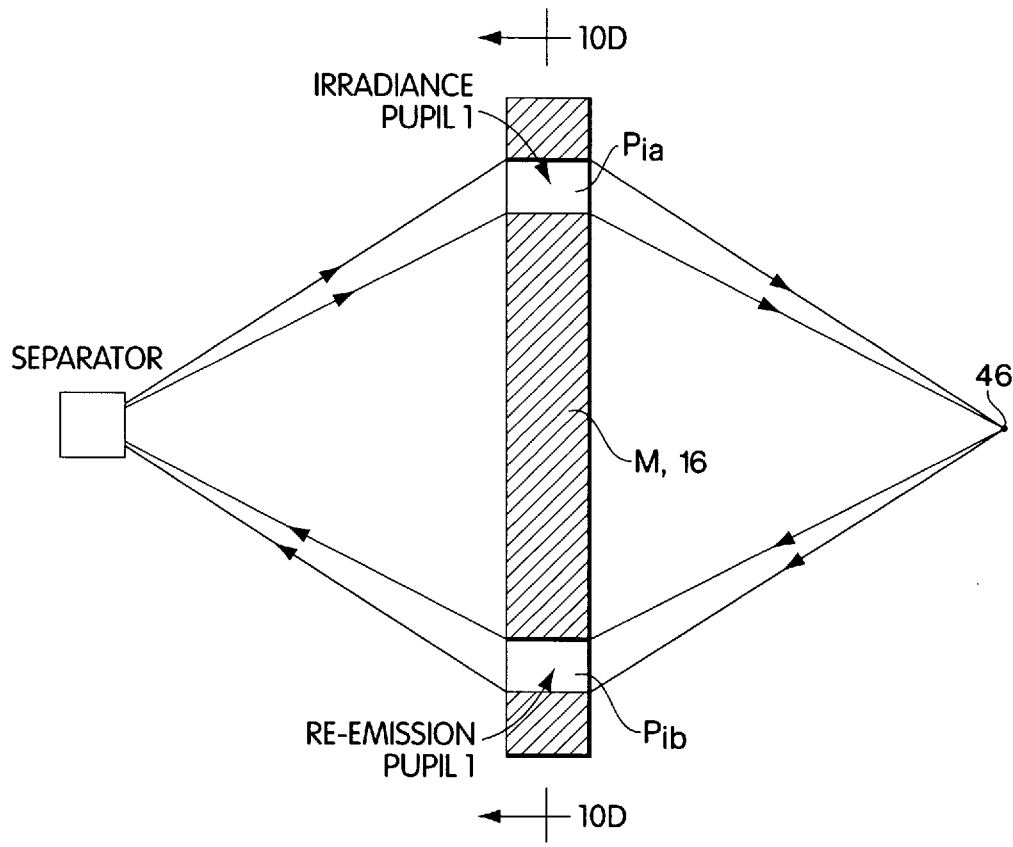
Figure 10D:
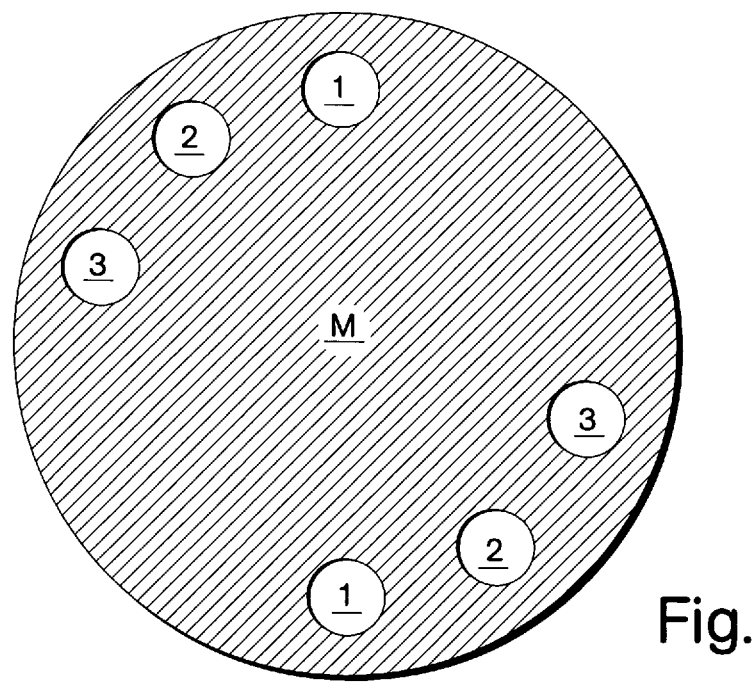

Another useful embodiment employs multiple apertures or pupils in the objective assembly, with the pupils arranged in spaced-apart pairs for illumination and detection. One such embodiment, shown in FIGS. 10C and 10D, makes maximum use of crossed beam asymmetry while also minimizing crosstalk. Rather than simply dividing the objective aperture into two parts where the adjacent partitions are less effective in enhancing depth resolution, a mask M in or on the objective 16 divides the pupil into a set of N diametrically opposed pairs of sub pupils (2N sub-pupils), $P_{1a}$, $P_{1b}$, ... $P_{Na}$, $P_{Nb}$ each pair being coupled to one self-conjugate field stop, such as the fiber-end field stops shown in FIGS. 9A and 9B. Here, crosstalk generated by scattering is reduced to a minimum, while the use of the full-diameter spacing of the objective 16 maximizes the depth resolution achievable by the crossed beams. The N pairs of pupils may be arranged in any desired distribution, and may simultaneously take N response readings. FIG. 10D shows the orientation of a pupil mask M which may be used to define the set of pupils on a lens. The single objective with a masked pupils can be replaced with individual objectives; this requires somewhat more complex alignment, but reduces the effects of aberrations. More important, the separate objective lenslets can be micro-lenses which adapt well to the spatial and focal constraints for a small instrument like an endoscope. These are preferred embodiments for an endoscope as described in FIG. 11 below.

Figure 10E:
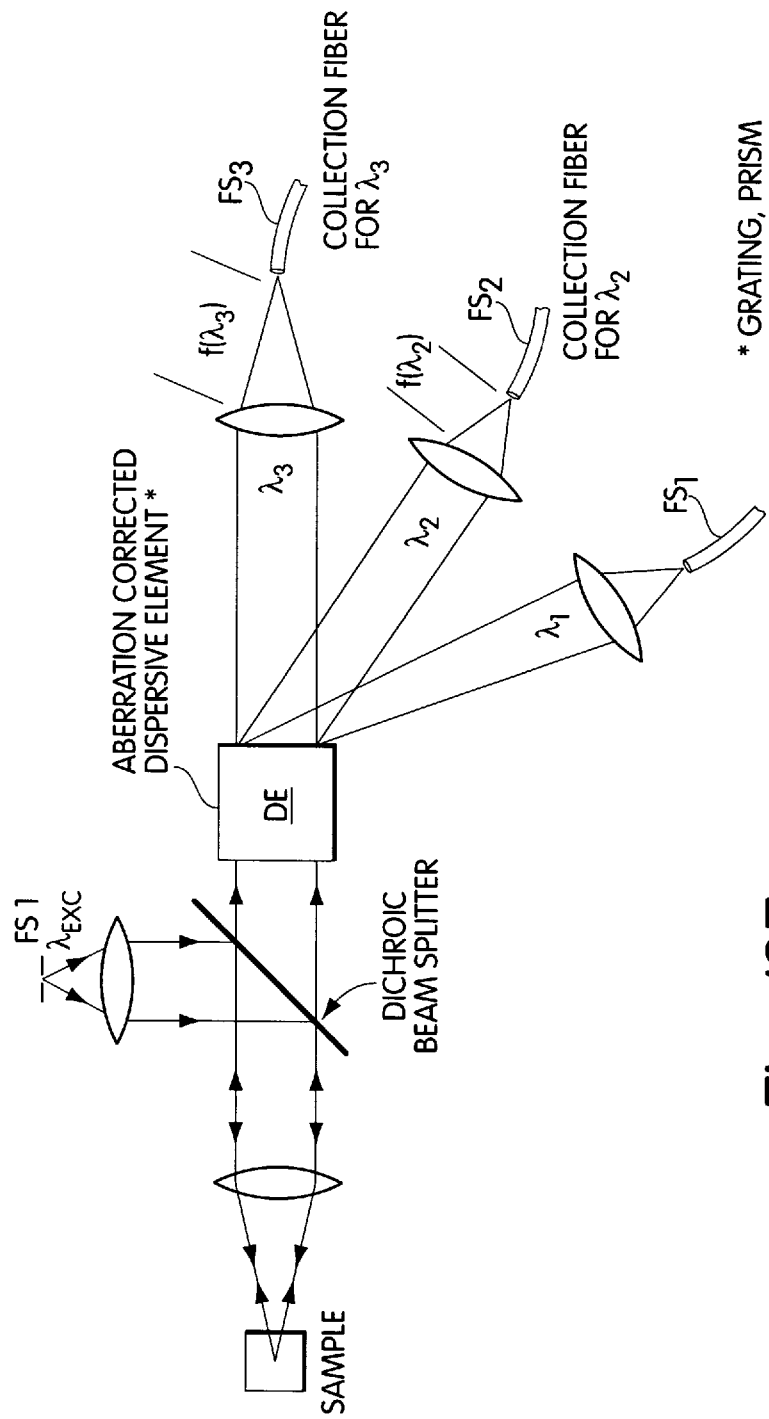

In yet another embodiment of the invention, a second or further field stop may be used in combination with a dispersive element to correct for residual chromatic aberrations of a holographic or refracting objective. Generally, the best available objectives for wide spectral bandwidth fluorescence confocal microscopy are well corrected chromatically. They form good images with constant magnification over ranges from about 300 nm to over 1,000 nm. However, even these superb lenses suffer from excessive "secondary spectrum" over a portion of that spectral range. Secondary spectrum is a wavelength-dependent shift of the axial position of an image with respect to the position of the lens. Even for large field stops, the shift of the image has two adverse effects: (1) the out of focus bundle of rays emanating from the displaced image rapidly becomes larger than the field stop diameter and energy is lost, and (2) loss of confocal conditions (conjugations of $FS_1$, and $FS_2$) leads to reduction in discrimination against background and depth sectioning capabilities. Partially for this reason, the previously described systems rely on reflective objectives in our wide-spectral-bandwidth systems. However, by using a dispersing element as part of the beam separator, one can then place secondary field stops $FS_i$ at the correct locations to be conjugate to the first field stop. As shown in FIG. 10E, an aberration-corrected dispersive element DE may be used to disperse the collected light into separate beam locations for each $\lambda_i$. These separate beams $\lambda_i$ are then each coupled into a corresponding fiber end $FS_i$, which serves as a secondary field stop located at the correct conjugate position for each $\lambda_i$. The dispersive element may, for example, be a holographically-formed element, a prism, or a classical transmission or reflection grating.

Figure 11A:
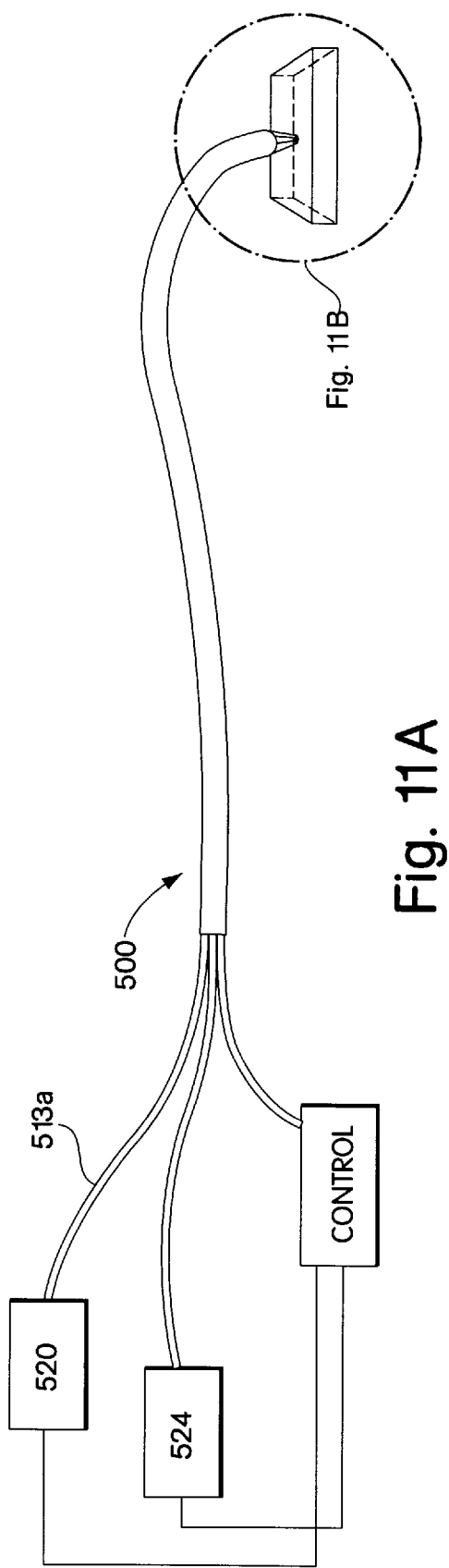
FIGS. 11A and 11B illustrates an endoprobe embodiment.
Figure 11B:
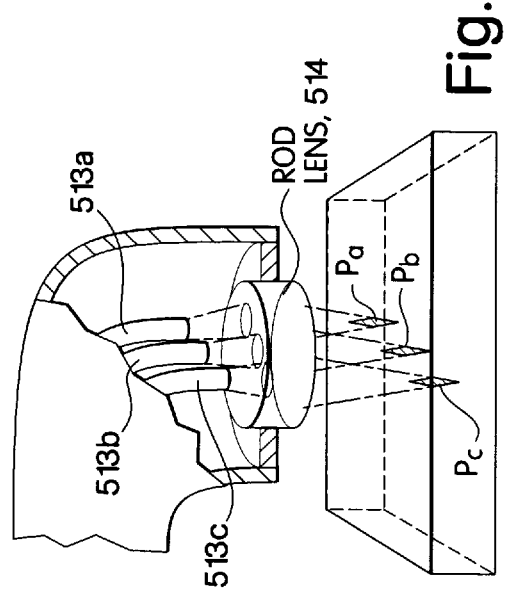

Yet another embodiment of a probe in accordance with the present invention may be employed in endoscopes and other contact or internal remote sensing applications. Such an embodiment is illustrated in FIG. 11. In this embodiment, an illumination fiber and a reception fiber each pass through an elongated body 500, which may be a conventional catheter, to an imaging head 510 which resides at the tip of the body or catheter. Tip 510 may include active focusing optics, for example, one or more rod lenses which are adapted to move to adjust probe volume depth. However preferably, the endoscope embodiment employs a multifiber arrangement, for example one such as shown in FIG. 9A, to define different probe volumes by simply applying a light input to different ones of the illumination fibers 513a, ..., externally of the device without requiring motion of any optics within the imaging head itself. Such an assembly may be rigidly and fully encapsulated to provide a smooth curved contact face that is brought into contact with the tissue surface in order to project to and collect light from different stations below the surface. For applications where wide spectral bandwidth is not essential, radially graded index of refraction rods (GRIN lenses) advantageously may terminate or follow the fibers to allow very simple optical alignment and short focal distances to be obtained in geometries suitable for endoscopic manipulation against tissue in a human body. The FIGURE illustrates one such lens 514 positioned for focusing the light from the plurality of helically-arranged input fibers 513a, 513b, 513c.

In each of the above embodiments, the probe volume is defined by the intersection of illumination and imaging beams in a manner to provide large signal strength while effectively discriminating against stimulation, scattering, reflection and luminescence and collection of light from the shadow region of tissue. A large illumination stop effectively provides the desired level of illumination in the probe volume enabling meaningful spectral measurements to be taken.

Among the various embodiments of the invention, several constructions are particularly advantageous. These include embodiments wherein the illumination and collecting optics are reflective, or catadioptic, and alleviate spectral aberrations. They also include apparatus in which the illuminating and collecting field stops are physically realized by the same element, and embodiments wherein the collected beam is physically separated from the illumination beam path after it has passed back through the common field stop. Another such construction employs a multimode fiber as the illumination field stop. One particularly advantageous device for probing localized subvolumes which can be varied in position achieves this by controlled translation of the field stops along respective beam axes of the illumination and collecting optics. This may also be achieved by translation of the objectives along their respective optical axes.

While the invention has been shown and described with reference to specific preferred embodiments, and several exemplary methods of use, those skilled in the art will understand that variations in form and detail may be made without departing from the spirit and scope of the invention. Indeed, having described the invention, further modifications or variations will occur to those skilled in the art, and such modifications and variations are understood to be within the scope of the invention, as defined by the claims appended hereto.

What is claimed is new and secured by Letters Patent is:

1. An analytic device for optical evaluation of a sample of material wherein the sample is at least partially transmissive and has an exposed face, such device comprising first means for directing illumination at the exposed face to illuminate said sample with light wherein said first means includes a first field stop of a size larger than diffraction-limited resolution of said first means at said first field stop second means for collecting light wherein said second means includes a second field stop larger than diffraction—limited resolution of said second means at said second field stop, and means for detecting illumination collected by the second means and producing a record therefrom wherein the first and the second means are arranged in a configuration such that the first and second field stops are at least partially conjugated through a common region in said sample and such that the record corresponds to an optical response that selectively represents light emanating from a volume element containing said common region responsive to said illumination while substantially excluding light emanating from outside said volume element.

2. An analytic device according to claim 1, wherein said volume element is sized or shaped to lie within a region of one tissue type or structure and the device discriminates against light from adjacent tissue type or structures.

3. An analytic device according to claim 1, further comprising memory means for storing a TRANSFORM T which correlates optical response information with a property P, and means for applying the stored transform T to optical response records produced by the detector, so that the device identifies the property P if present in the volume element examined.

4. An analytic device according to claim 3, wherein the optical response is a spectral response and the detector produces records representative of collected light amplitude at a number n of wavelength bands and the stored transform T has a dimension n, where n is an integer.

5. An analytic device according to claim 4, wherein the device applies the stored transform T to identify m properties, where m is an integer.

6. An analytic device according to claim 3, wherein the detector produces spectral response records representative of collected light amplitude at a number n of wavelength bands and the stored transform T has a dimension mn, where m is an integer $\geq 2$.

7. An analytic device according to claim 4, wherein the device applies the stored transform to identify m properties P.

8. An analytic device according to claim 5, wherein the device applies the stored transform to identify p properties P, where p is an integer not equal to m.

9. An analytic device for measurement of a condition of matter in its natural environment, such device comprising means for illuminating a specimen of matter and collecting an optical response from the specimen in its natural environment with weakly confocal optics, such that the optical response is collected with non-imaging resolution and derives substantially and preferentially from a localized subvolume within said specimen, and means for detecting and digitizing the optical response to represent the response as a plurality of values for different wavelengths.

10. The analytic device of claim 9, further comprising means for storing a transform derived from correlations of natural environment optical responses of a training set and independent evaluations of a condition prevailing in material from which said responses were obtained, and processing means for applying the stored transform to the plurality of values from the specimen to produce an output thereby identifying the condition.

11. The analytic device of claim 9, wherein the localized subvolume has a cross-dimension between ten micrometers and three millimeters, and the device is coupled to an optical medical examination instrument (such as a colposcope, endoscope or laparoscope) for viewing the specimen as said optical responses are collected.

12. The analytic device of claim 9, embodied in an endoscope and having a positioning face, wherein said means for illuminating and collecting collects a response from a subvolume at a defined position with respect to the positioning face.

13. The analytic device of claim 12, wherein the subvolume is an asymmetric volume alignable with a tissue feature and having a shape selected from the set comprising sliver, cone, meniscus, plug and intersection of a conic.

14. The analytic device of claim 9, wherein the natural environment is a living tissue environment and said means for collecting strongly discriminates such that noise caused by integrated contribution to said optical response, from outside the localized volume element in the living tissue, amounts to less than half of the optical response from inside the localized volume element.

15. The analytic device of claim 9, wherein the natural environment is a living tissue environment and said means for collecting strongly discriminates such that an identifiable and reproducible optical response is collected from said volume element.

16. The analytic device of claim 15, wherein the means for illuminating and collecting defines said subvolume localized along an axis of tissue depth.

17. The analytic device of claim 9, wherein the means for illuminating and collecting collects a response from a localized subvolume of a size to faithfully represent at least one of (i) a layer of tissue to the substantial exclusion of underlying or overlying tissue, and (ii) a submacroscopic volume of tissue to the substantial exclusion of adjacent tissue.

18. The analytic device of claim 14, further including means for scanning to sample localized volume elements distributed across said tissue for developing a profile of optical responses in said tissue.

19. The analytic device of claim 9, wherein the means for illuminating and collecting directs illumination wherein diffraction effects are negligible and collects a response to illumination in a non-imaging manner from a volume element having a cross-dimension of between ten micrometers and three millimeters in said matter.

20. An analytic device for detecting spectral data from tissue, comprising
    means for directing illumination into the tissue with a first intensity distribution in said tissue that drops off substantially monotonically away from a first region in a first optical path
    means for collecting light emanating therefrom with an efficacy of collection distribution that drops off substantially monotonically away from a second region in a second optical path,
    the illumination and collecting being aligned so that the first path and the second path overlap in a non-pointlike volume element corresponding in one dimension to a tissue feature of interest, such that the collected light selectively represents an optical response to said illumination of said tissue feature of interest, while preferentially excluding light from surrounding tissue, and
    a detector operating on the collected light to produce an optical response, wherein said optical response indicates a condition prevailing in said volume element.

21. The analytic device of claim 20, wherein the first path and the second path overlap such that the collected optical response of said element is identifiable and reproducible.

22. The analytic device of claim 20, wherein the optical response is a digitized spectral response represented as a set $\{a_i(\lambda_i)\}$ where $a_i$ are values of irradiance in respective bands around wavelength $\lambda_i$, and $i \geq 2$.

23. An analytic device for optical evaluation of a sample of material, such device comprising,
    a light source for providing light,
    a first field stop which selectively transmits at least a portion of said light,
    optical means for directing said portion to illuminate a volume of a sample,
    optical collection means for collecting radiation emanating from the illuminated volume of the sample,
    a second field stop which selectively transmits at least a portion of said collected light, said second field stop being at least partially conjugated to said first field stop through a common volume element of illuminated and observed volumes
    detecting means for detecting light passed by the second field stop, said detecting means thereby detecting light collected from said volume element and producing a signal indicative thereof,
    wherein a geometric image of the first field stop defined by the optical means encompasses effectively all of the radiation selectively passed by the first field stop so that as said device is directed at a selected target volume element in the sample, an integrated contribution from light emanating outside of the target volume element is small and the signal produced by the detecting means selectively and preferentially characterizes the optical response of the target volume element.

24. An analytic device according to claim 1, further comprising means for analyzing the record from said volume element to characterize at least one property of the volume element.

25. An analytic device according to claim 10, further comprising means for storing data $\{d\}$ representative of extrinsic observations pertaining to the specimen and wherein the transform is derived at least in part from such extrinsic observations pertaining to the training set, and the processing means applies the transform to at least a portion of the data $\{d\}$.

* * * * *